(12) United States Patent
Okada et al.

(10) Patent No.: US 11,883,183 B2
(45) Date of Patent: Jan. 30, 2024

(54) COGNITIVE FUNCTION EVALUATION DEVICE, COGNITIVE FUNCTION EVALUATION METHOD, AND RECORDING MEDIUM

(71) Applicant: PANASONIC INTELLECTUAL PROPERTY MANAGEMENT CO., LTD., Osaka (JP)

(72) Inventors: Takashi Okada, Tokyo (JP); Yoshihiro Matsumura, Osaka (JP); Takashi Nishiyama, Hyogo (JP); Kengo Abe, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 307 days.

(21) Appl. No.: 16/339,683

(22) PCT Filed: Sep. 27, 2017

(86) PCT No.: PCT/JP2017/034843
§ 371 (c)(1),
(2) Date: Apr. 4, 2019

(87) PCT Pub. No.: WO2018/066422
PCT Pub. Date: Apr. 12, 2018

(65) Prior Publication Data
US 2020/0008735 A1 Jan. 9, 2020

(30) Foreign Application Priority Data
Oct. 7, 2016 (JP) .................................. 2016-199499

(51) Int. Cl.
*A61B 5/00* (2006.01)
*A61B 5/11* (2006.01)
(Continued)

(52) U.S. Cl.
CPC .......... *A61B 5/4088* (2013.01); *A61B 5/0002* (2013.01); *A61B 5/1113* (2013.01);
(Continued)

(58) Field of Classification Search
CPC ..... A61B 5/112; A61B 5/4088; A61B 5/4845; A61B 5/1124; A61B 5/165; A61B 5/11;
(Continued)

(56) References Cited

U.S. PATENT DOCUMENTS

2010/0298661 A1* 11/2010 McCombie ........ A61B 5/02028
600/301
2012/0101411 A1 4/2012 Hausdorff et al.
(Continued)

FOREIGN PATENT DOCUMENTS

JO H09-168529 A 6/1997
JP H09-168529 A 6/1997
(Continued)

OTHER PUBLICATIONS (Translated) KR 101205908 B1 (Konkuk University Industrial Cooperation Corp [KR]), Nov. 28, 2012 (Nov. 28, 2012) (Year: 2012).*
(Continued)

*Primary Examiner* — Sean P Dougherty
*Assistant Examiner* — Jonathan E. Cooper
(74) *Attorney, Agent, or Firm* — Rimon, P.C.

(57) ABSTRACT

Cognitive function evaluation device includes: storing unit storing reference data on the relationship between the periodicity of a body movement of a person walking and the cognitive function level of the person; acquiring unit that acquires body movement data on the detected body movement from body movement sensor that detects the body movement of subject walking; and calculating unit that calculates the periodicity of the body movement while (Continued)

walking from the acquired body movement data and checks the calculated periodicity against reference data stored in storing unit so as to identify the cognitive function level corresponding to the calculated periodicity.

7 Claims, 17 Drawing Sheets

(52) U.S. Cl.
CPC ........... *A61B 5/1118* (2013.01); *A61B 5/6802* (2013.01); *A61B 5/6823* (2013.01); *A61B 2562/0219* (2013.01)

(58) Field of Classification Search
CPC ... A61B 5/1123; A61B 5/1101; A61B 5/1118; A61B 2562/0219; A61B 5/6823; A61B 5/0002
USPC ........................................................ 600/595
See application file for complete search history.

(56) References Cited

U.S. PATENT DOCUMENTS

| | | | |
|---|---|---|---|
| 2012/0209149 A1 | 8/2012 | Yoneyama et al. | |
| 2014/0024971 A1* | 1/2014 | Bunn | A61B 5/1124 600/595 |
| 2014/0276130 A1* | 9/2014 | Mirelman | A61B 5/112 600/595 |
| 2015/0112899 A1* | 4/2015 | Dagum | G06N 5/022 706/12 |
| 2015/0208975 A1* | 7/2015 | Ghajar | G16H 40/63 600/595 |
| 2016/0345870 A1 | 12/2016 | Ichikawa et al. | |
| 2018/0192917 A1 | 7/2018 | Piijl et al. | |
| 2020/0037942 A1* | 2/2020 | Howard | A61B 5/4088 |
| 2021/0223282 A1* | 7/2021 | Tseng | G01C 19/5712 |

FOREIGN PATENT DOCUMENTS

| | | | | |
|---|---|---|---|---|
| JP | 2002-345786 A | 12/2002 | | |
| JP | 2010-005033 A | 1/2010 | | |
| JP | 2011-092696 A | 5/2011 | | |
| JP | 2012-024275 A | 2/2012 | | |
| JP | 2013-059489 A | 4/2013 | | |
| JP | 5332292 B2 | 11/2013 | | |
| JP | 2013-255786 A | 12/2013 | | |
| JP | 5417204 B2 | 2/2014 | | |
| JP | 2014-142746 A | 8/2014 | | |
| JP | 2015-066155 A | 4/2015 | | |
| JP | 2016-022310 A | 2/2016 | | |
| KR | 101205908 B1 * | 11/2012 | ........... | A61B 5/0006 |
| WO | WO-2014181603 A1 * | 11/2014 | ........... | A61B 5/1122 |
| WO | 2015/129883 A1 | 9/2015 | | |
| WO | 2015/169880 A1 | 11/2015 | | |
| WO | WO-2016156867 A1 * | 10/2016 | ........... | A61B 5/0002 |

OTHER PUBLICATIONS

Susumu Ito, et al., "Main Nerve Syndrome of Dementia Disorder; in particular, Normal Pressure Hydrocephalus Focusing on Gait Disorder", Japanese journal of geriatric psychiatry, vol. 18, No. 1, Jan. 2007, pp. 55-59 with English Translation.

International Search Report and Written Opinion dated Jan. 9, 2018 in International Application No. PCT/JP2017/034843; with partial English translation.

Hsu Y.-L. et al., "Gait and Balance Analysis for Patients With Alzheimer's Disease Using an Inertial-Sensor-Based Wearable Instrument." IEEE Journal of Biomedical and Health Informatics, Jun. 2, 2014, vol. 18, No. 6, pp. 1822-1830.

Search Report and Written Opinion dated Jul. 23, 2020 for the corresponding Singaporean patent application No. 11201902960Q.

* cited by examiner

FIG. 10

```
START
  ↓
S10  ACQUIRE ACCELERATION DATA
  ↓
S11  CALCULATE WINDOW FUNCTION
  ↓
S12  DETERMINE FOURIER TRANSFORM RANGE
  ↓
S13  PERFORM FOURIER TRANSFORM ON ACCELERATION DATA TO CALCULATE FREQUENCY SPECTRUM
  ↓
S14  STANDARDIZE FREQUENCY SPECTRUM WITH MAXIMUM PEAK INTENSITY
  ↓
S15  INTEGRATE HIGH-FREQUENCY COMPONENTS OF STANDARDIZED FREQUENCY SPECTRUM
  ↓
END
```

FIG. 11

|  | NORMAL CONTROLS (NC) | MILD COGNITIVE IMPAIRMENT (MCI) | ALZHEIMER'S DISEASE (AD) |
|---|---|---|---|
| NUMBER OF SUBJECTS | 90 | 94 | 93 |
| MoCA AVERAGE SCORE | 27.4 | 22.1 | 16.2 |
| MoCA SCORE RANGE | 25.2 - 29.6 | 19.0 - 25.2 | 21.0 - 11.4 |

COGNITIVE FUNCTION EVALUATION DEVICE, COGNITIVE FUNCTION EVALUATION METHOD, AND RECORDING MEDIUM

CROSS-REFERENCE OF RELATED APPLICATIONS

This application is the U.S. National Phase under 35 U.S.C. § 371 of International Patent Application No. PCT/JP2017/034843, filed on Sep. 27, 2017, which in turn claims the benefit of Japanese Application No. 2016-199499, filed on Oct. 7, 2016, the entire disclosures of which Applications are incorporated by reference herein.

TECHNICAL FIELD

The present invention relates to a cognitive function evaluation device, a cognitive function evaluation method, and a recording medium.

BACKGROUND ART

A system and the like are proposed to evaluate the probability of geriatric diseases such as a knee pain based on parameters measured from human walking. For example, a system is provided to measure the step lengths of a person and the like, determine the risk of falls or the ability to walk, and support the prevention of a fall of a person. Regarding geriatric diseases other than falls, the risk of geriatric diseases is easily evaluated from walking in an evaluation method (for example, see Patent Literature (PTL) 1).

In the evaluation method described in PTL 1, the probability of geriatric diseases is evaluated based on walking parameters measured from human walking. The walking parameters include a walking ratio, a step length, and an interval of walking. Geriatric diseases such as a knee pain and a lower back pain are evaluated in this method.

Thus, the risk of geriatric diseases other than falls can be easily evaluated from walking in the evaluation method described in PTL 1.

CITATION LIST

Patent Literature

PTL 1: Japanese Unexamined Patent Application Publication No. 2013-255786

SUMMARY OF THE INVENTION

Technical Problem

In the evaluation method described in PTL 1, however, a sheet-type pressure sensor is used to measure the walking parameters and thus the probability of geriatric diseases cannot be easily evaluated. Thus, it takes a long time to evaluate the probability of geriatric diseases.

The present invention provides, for example, a cognitive function evaluation device and the like that can quickly evaluate a cognitive function.

Solutions to Problem

A cognitive function evaluation device according to an aspect of the present invention includes: a storing unit storing reference data on the relationship between the periodicity of a body movement of a person walking and the cognitive function level of the person; an acquiring unit that acquires body movement data on a detected body movement from a body movement sensor that detects the body movement of a subject walking; and a calculating unit that calculates the periodicity of the body movement from the acquired body movement data and checks the calculated periodicity of the body movement against the reference data stored in the storing unit so as to identify the cognitive function level corresponding to the calculated periodicity of the body movement.

A cognitive function evaluation method according to an aspect of the present invention includes the steps of: acquiring body movement data on the detected body movement from a body movement sensor that detects the body movement of a subject walking; and calculating the periodicity of the body movement from the acquired body movement data and identifying a cognitive function level corresponding to the calculated periodicity of the body movement by checking the calculated periodicity of the body movement against reference data that is stored in the storing unit and indicates the relationship between the periodicity of the body movement of a person walking and the cognitive function of the person.

The present invention may be implemented as a non-transitory computer-readable recording medium having recorded thereon a program that enables a computer to perform the steps included in the cognitive function evaluation method.

Advantageous Effect of Invention

The cognitive function evaluation device and the like according to the aspect of the present invention can quickly evaluate a cognitive function.

BRIEF DESCRIPTION OF DRAWINGS

FIG. 10 is a flowchart showing the steps of calculating an integral from the acceleration data by the cognitive function evaluation device according to Embodiment 1.

FIG. 11 shows scores obtained when MoCA tests were conducted on subjects.

DESCRIPTION OF EXEMPLARY EMBODIMENTS

Figure 1:
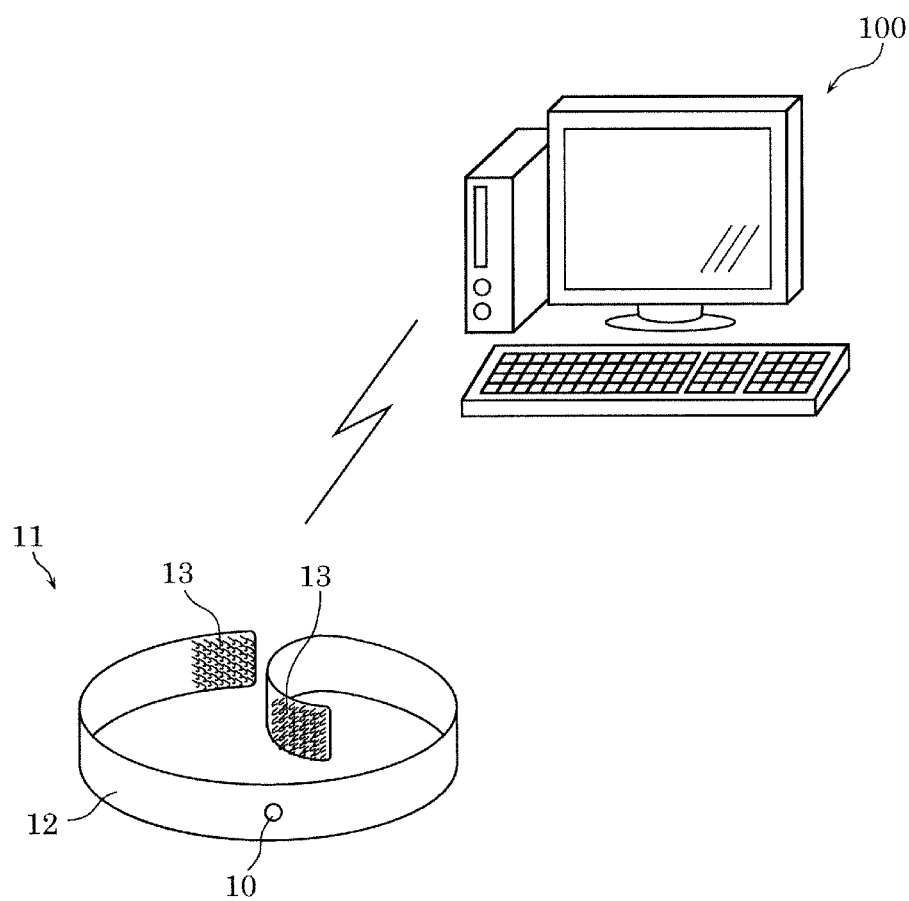
FIG. 1 illustrates a system configuration including a cognitive function evaluation device according to Embodiment 1.

A cognitive function evaluation device and a cognitive function evaluation method according to embodiments will be described below with reference to the accompanying drawings. All the following embodiments illustrate general and specific examples. Numerical values, shapes, materials, constituent elements, the layout and connection pattern of the constituent elements, steps, and the order of steps in the following embodiments are merely exemplary and are not aimed at limiting the present invention. In the following embodiments, constituent elements not described in the independent claims illustrating the most generic concept will be illustrated as optional constituent elements.

The drawings are schematic views that are not strictly illustrated. Substantially the same configurations in the drawings are indicated by the same reference numerals and the redundant explanation thereof may be omitted or simplified.

In the present specification, Z-axis direction will be referred to as the walking direction of a person (longitudinal direction). The negative direction along Z axis is defined as the walking direction of a subject. Moreover, Y-axis direction will be referred to as a perpendicular direction (vertical direction). The positive direction along Y axis is defined as the vertically upward direction of the subject. Furthermore, X-axis direction will be referred to as a horizontal direction (lateral direction) orthogonal to the walking direction of the subject. The forward direction along X axis is defined as the right direction viewed from the subject.

Embodiment 1

[The Configuration of a Cognitive Function Evaluation Device]

The configuration of a cognitive function evaluation device according to Embodiment 1 will be first described below. FIG. 1 illustrates a system configuration including a cognitive function evaluation device according to Embodiment 1.

Cognitive function evaluation device 100 is a device for identifying the cognitive function level of a subject by measuring the body movement of a person walking. A cognitive function means the capability of cognition, memorization, and decision. In a specific example, cognitive function evaluation device 100 evaluates whether a person has a symptom of dementia (dementia patient). Dementia indicates a deterioration of the cognitive function. A specific example of dementia is Alzheimer's disease (AD). Dementia has no obvious symptoms at first and thus conventionally a dementia patient sees a doctor after a family member or a third party urges the patient to have an examination at a hospital. Moreover, a subject undergoes a batch test, e.g., a MoCA (Montreal Cognitive Assessment) test for a diagnosis of dementia, thereby confirming whether the subject has dementia or not. However, it takes about 15 minutes to conduct the MoCA test. Furthermore, in order to decide whether the subject has dementia or not, it is necessary to conduct the MoCA test every few days so as to diagnose the change in the subject over time. In short, the MoCA test requires a long period to diagnose whether the subject has dementia or not. It is known that the body movement of a dementia patient walking is different from that of a person who does not have dementia (person in good health).

The inventors have found that the cognitive function level of a subject is identified by evaluating the body movement of the subject walking according to a predetermined method. Specifically, cognitive function evaluation device 100 according to the present embodiment is a device for quickly identifying the cognitive function level of a subject by measuring the body movement of the subject walking.

Subsequently, an attachment will be discussed as a specific example of a device for measuring the body movement of the subject walking.

As shown in FIG. 1, attachment 11 includes acceleration sensor 10, strap 12, and hook-and-loop fastener 13.

Attachment 11 is, for example, a belt attached to the waist of the subject. The hook side and the loop side of hook-and-loop fastener 13 are joined at an appropriate position so as to adjust the length of strap 12. Specifically, strap 12 is wound around the waist of the subject and is fastened with a properly adjusted length, thereby attaching attachment 11 to the waist of the subject. Means for adjusting the length of strap 12 is not limited to hook-and-loop fastener 13. Fasters such as a buckle may be used instead. Attachment 11 may not be a belt but clothes worn by the subject. For example, acceleration sensor 10 can be fixed to the clothes or may be stored in a pocket of the clothes.

Acceleration sensor 10 is attached to the subject and measures acceleration data as a specific example of body movement data indicating the body movement of the subject walking. Specifically, according to a predetermined measurement rate, acceleration sensor 10 measures the acceleration of a part of the subject having acceleration sensor 10. The measurement rate is the number of measurements of acceleration per unit time. Acceleration sensor 10 transmits the measured acceleration data to cognitive function evaluation device 100.

In the case of a triaxial acceleration sensor, the acceleration data measured by acceleration sensor 10 is three-dimensional acceleration vector data, for example, acceleration data in the longitudinal direction, the lateral direction, and the vertical direction of the subject. The acceleration data includes a plurality of measurement points. The measurement points are each associated over time information that indicates a time when the measurement point is measured.

Acceleration sensor 10 transmits the measured acceleration data to cognitive function evaluation device 100. Specifically, attachment 11 includes a radio communication device (not shown) and communicates with cognitive function evaluation device 100 via the radio communication device. Acceleration sensor 10 transmits the measured acceleration data to cognitive function evaluation device 100 via radio communications. Radio communications are conducted based on predetermined radio communications standards, for example, Bluetooth (registered trademark), Wi-Fi (registered trademark), and ZigBee (registered trademark).

Figure 2:
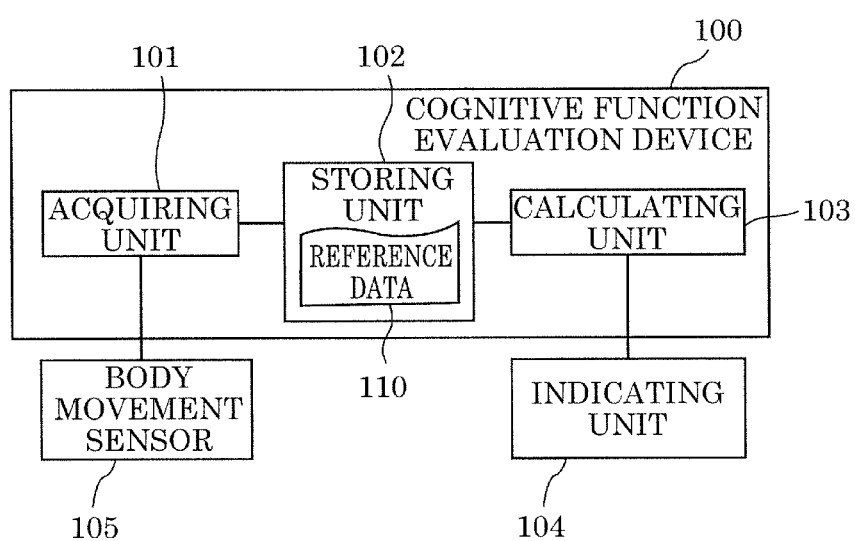
FIG. 2 is a block diagram illustrating the characteristic functional configuration of the cognitive function evaluation device according to Embodiment 1.

FIG. 2 is a block diagram illustrating the characteristic functional configuration of cognitive function evaluation device 100 according to Embodiment 1. As illustrated in FIG. 2, cognitive function evaluation device 100 includes acquiring unit 101, storing unit 102, and calculating unit 103.

Acquiring unit 101 is a processing unit that acquires body movement data on the subject measured by body movement sensor 105. Acquiring unit 101 is implemented by, for example, a CPU (Central Processing Unit), control programs stored in storing unit 102, and a communication interface.

Storing unit 102 is memory that stores the body movement data acquired by acquiring unit 101. Storing unit 102 includes, for example, ROM (Read Only Memory), RAM (Random Access Memory), or an HDD (Hard Disk Drive). Moreover, storing unit 102 stores reference data 110 to be checked by calculating unit 103 against the body movement data acquired by acquiring unit 101. Reference data 110 will be specifically discussed later.

Calculating unit 103 is a processing unit that calculates a cognitive function evaluation result from the body movement data acquired by acquiring unit 101. Specifically, calculating unit 103 calculates the periodicity of a body movement from the body movement data acquired by acquiring unit 101 and checks the calculated periodicity of the body movement against reference data 110 stored in storing unit 102. The periodicity of the body movement indicates periodic vibrations generated while human walking. The periodicity of the body movement will be specifically discussed later. Moreover, calculating unit 103 identifies the level of the cognitive function of the subject based on the periodicity of the body movement and reference data 110.

Cognitive function evaluation device 100 may be connected so as to be communicable with body movement sensor 105 and indicating unit 104.

Body movement sensor 105 is a sensor for detecting a body movement of the subject walking. Body movement sensor 105 is, for example, acceleration sensor 10, a camera (image sensor), or a radio wave sensor.

Indicating unit 104 is a display device for notifying subject 2 of the evaluation result indicating the cognitive function level, the evaluation result being identified by calculating unit 103. Indicating unit 104 is, for example, a display. Calculating unit 103 may control indicating unit 104 so as to display the evaluation result indicating the cognitive function level.

Figure 3:
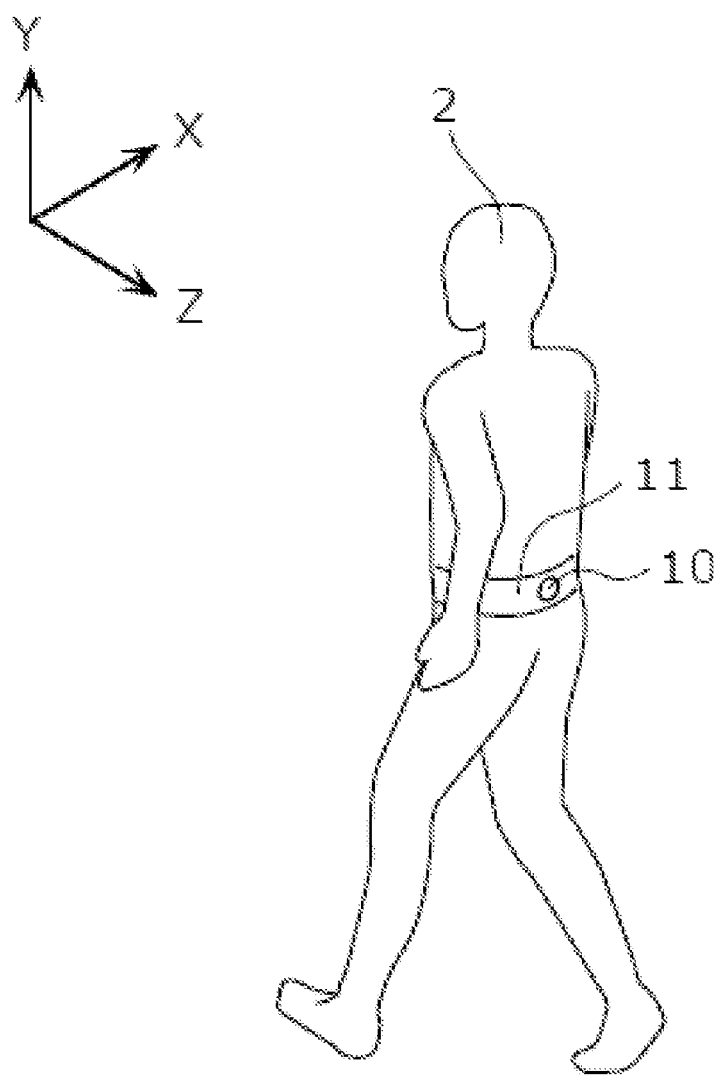
FIG. 3 shows that a subject wears an attachment having an acceleration sensor according to Embodiment 1.

FIG. 3 shows that the subject wears attachment 11 having acceleration sensor 10 according to Embodiment 1.

As shown in FIG. 3, acceleration sensor 10 provided on attachment 11 is attached to the lower back of subject 2. Acceleration sensor 10, which is an example of body movement sensor 105, is not always attached to the waist on the back of subject 2 and may be attached to, for example, the waist on the front side, the head, the chest, the leg, or the arm of subject 2.

Figure 4:
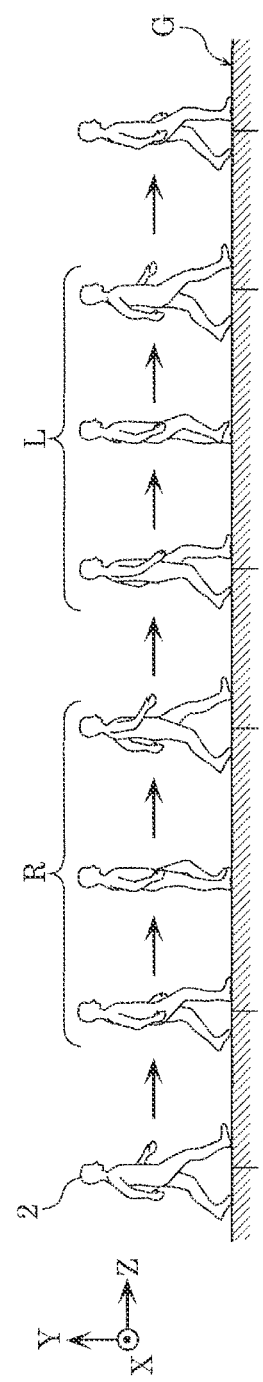
FIG. 4 illustrates an image of the representative actions of a person walking.

Human walking includes representative actions and has periodicity. FIG. 4 illustrates an image of the representative actions in the periodicity of walking.

As shown in FIG. 4, the state of right foot axis R and the state of left foot axis L are alternately repeated while human walking. In other words, the state of right foot axis R and the state of left foot axis L are alternately repeated so as to exhibit predetermined periodicity while walking. A walking period is a repetition period from one action to the same action while walking. For example, a walking period is a period from a touch of the left heel on ground G to another touch of the left heel on ground G. In the present specification, the period is regarded as two steps. Specifically, a period from a touch of the left heel on the ground to a touch of the right heel on ground G is regarded as one step.

In this case, when the left foot of subject 2 is in contact with ground G, subject 2 has left foot axis L, that is, the center of gravity on the left foot. Thus, the waist of subject 2 moves to the left. In short, the posture of subject 2 moves to the left. In other words, the center of gravity of subject 2 is located on the left relative to the center of gravity of subject 2 in an upright posture.

Similarly, when the right foot of subject 2 touches ground G, subject 2 has right foot axis R, that is, the center of gravity on the right foot. Thus, the waist of subject 2 moves to the right. In short, the posture of subject 2 moves to the right. In other words, the center of gravity of subject 2 is located on the right relative to the center of gravity of subject 2 in an upright posture.

In this way, the period of right foot axis R with the center of gravity on the right foot of subject 2 and the period of left foot axis L with the center of gravity on the left foot of subject 2 are repeated when a person is walking.

Example

The acceleration data will be discussed below. The acceleration data is acquired as a specific example of body movement data by acceleration sensor 10 acting as body movement sensor 105.

Figure 5:
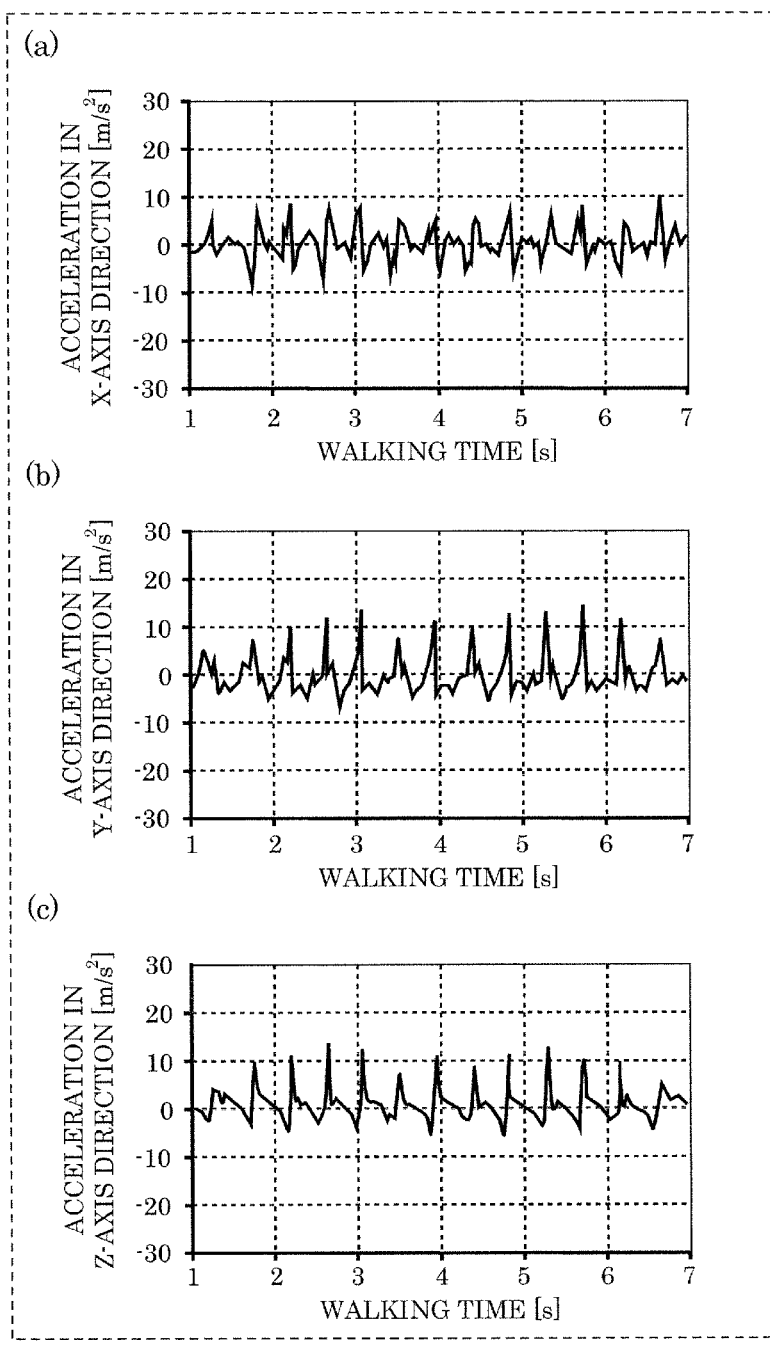
FIG. 5 shows an example of acceleration data acquired by the cognitive function evaluation device according to Embodiment 1.

FIG. 5 shows an example of the acceleration data acquired by cognitive function evaluation device 100 according to Embodiment 1. Specifically, FIG. 5 shows the acceleration data acquired when subject 2 who wears attachment 11 with acceleration sensor 10 (triaxial acceleration sensor) walks in the negative direction of Z axis as shown in FIG. 3. Acceleration sensor 10 is a specific example of body movement sensor 105. In other words, the acceleration data in FIG. 5 indicates the change in the acceleration of the body movement of subject 2 over time when subject 2 is walking. In FIG. 5, the vertical axis of the acceleration data indicates an acceleration and the horizontal axis of the acceleration data indicates a walking time. The acceleration data in FIG.

5(*a*) indicates an acceleration in the X-axis direction of subject 2. The acceleration data in FIG. 5(*b*) indicates an acceleration in the Y-axis direction of subject 2. The acceleration data in FIG. 5(*c*) indicates an acceleration in the Z-axis direction of subject 2.

As shown in FIG. 5, it can be confirmed that positive and negative accelerations in the acceleration data alternately change in all of X-axis direction, Y-axis direction, and Z-axis direction. Cognitive function evaluation device 100 analyzes the acceleration data so as to calculate the periodicity of the body movement of subject 2 walking.

Figure 6:
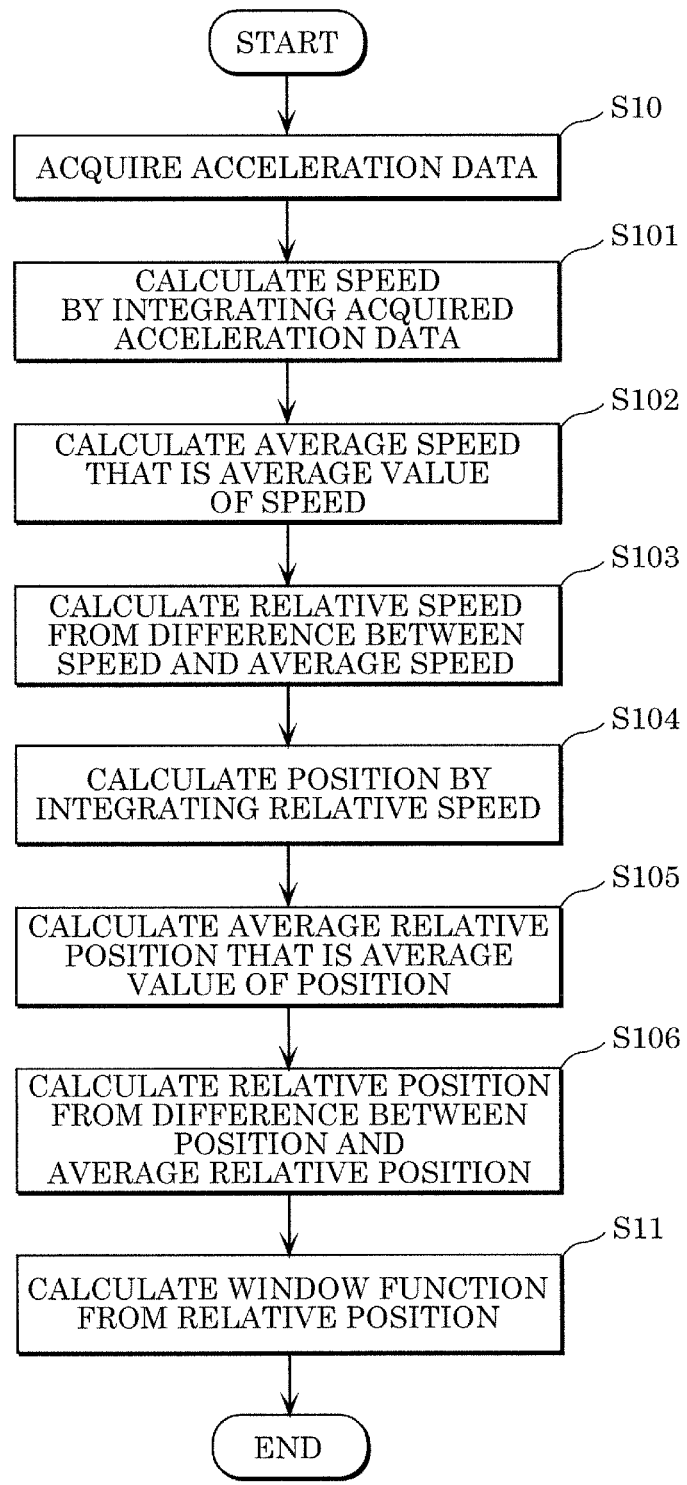
FIG. 6 is a flowchart showing the steps of calculating the relative position of the center of gravity of the subject from the acceleration data by the cognitive function evaluation device according to Embodiment 1.

FIG. 6 is a flowchart showing the steps of calculating the relative position of the center of gravity of subject 2 from the acceleration data by cognitive function evaluation device 100 according to Embodiment 1. Specifically, FIG. 6 shows the steps of measuring the acceleration data of subject 2 by acceleration sensor 10, which is a specific example of body movement sensor 105, acquiring the acceleration data by acquiring unit 101, and converting the acceleration data stored in storing unit 102 by calculating unit 103.

As shown in FIG. 6, calculating unit 103 acquires the acceleration data stored in storing unit 102 (step S10). Subsequently, calculating unit 103 calculates a speed by integrating the acquired acceleration data (step S101). Calculating unit 103 then calculates the average speed of subject 2, that is, the average value of the speed from the calculated speed (step S102). Thereafter, calculating unit 103 calculates a relative speed by determining a difference between the calculated speed and the calculated average speed (step S103). Calculating unit 103 then calculates the center of gravity position of subject 2 by integrating the calculated relative speed (step S104). Subsequently, calculating unit 103 calculates an average relative position, that is, the average value of the center of gravity position from the calculated center of gravity position of subject 2 (step S105). At this point, calculating unit 103 calculates a relative position by determining a difference between the calculated center of gravity position of subject 2 and the calculated average relative position (step S106). Calculating unit 103 then calculates a window function from the calculated relative position (step S11).

Figure 7:
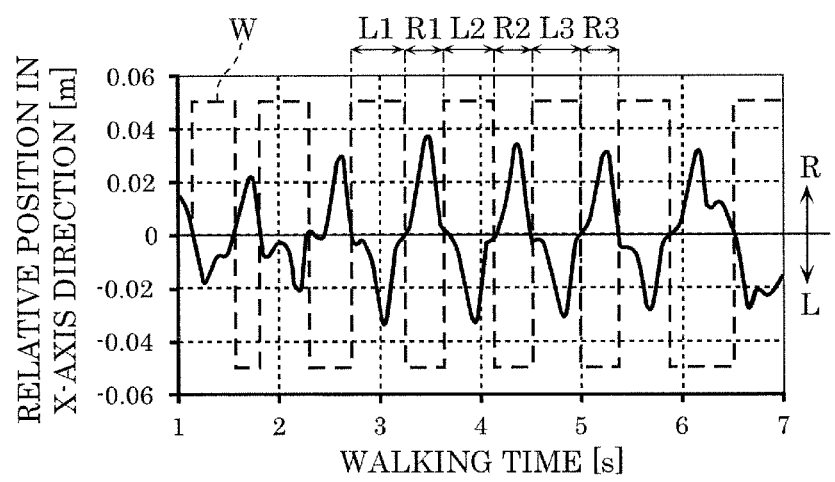
FIG. 7 shows data on the relative position of the subject and a window function, the relative position being calculated from the acceleration data acquired by the cognitive function evaluation device according to Embodiment 1.

FIG. 7 shows data on the relative position of subject 2 and the window function, the relative position being calculated from the acceleration data acquired by cognitive function evaluation device 100 according to Embodiment 1. Specifically, FIG. 7 shows relative position data on subject 2, the relative position data being acquired by converting the acceleration data in the X-axis direction of FIG. 5(*a*).

In FIG. 7, the horizontal axis of the graph indicates a walking time and the vertical axis of the graph indicates the center of gravity position of subject 2. In this case, the relative position is the displacement of the center of gravity position of subject 2 if the center of gravity of subject 2 in an upright posture is located at 0 immediately before subject 2 starts walking. Specifically, in Embodiment 1, acceleration sensor 10 is located such that the relative position of the center of gravity is 0 on the vertical axis when subject 2 stands in an upright posture immediately before starts walking.

As shown in FIG. 7, the relative position changes periodically in the positive direction and the negative direction. This proves that the center of gravity of subject 2 moves between the right foot (positive direction) and the left foot (negative direction) while walking. In other words, subject 2 alternately repeats the state of right foot axis R and the state of left foot axis L.

In this case, calculating unit 103 calculates window function W, which is indicated by a broken line in FIG. 7, from relative position data on subject 2, the relative position data being indicated by a solid line in FIG. 7. Window function W is a function calculated from relative position data with respect to the walking time of subject 2. Window function W is, for example, a rectangular window function that is set such that a point in a walking time at the relative position of 0 agrees with a point in a walking time when the maximum value and the minimum value of window function W are changed, in the relative position data with respect to a walking time. Thus, by determining whether window function W is the maximum value or the minimum value, whether subject 2 is placed in the state of right foot axis R or the state of left foot axis L can be easily calculated. In short, window function W is a function indicating the walking steps of subject 2. The maximum value and the minimum value of window function W may be set at any values.

Regarding window function W in FIG. 7, if window function W has the maximum value, subject 2 has the center of gravity on the left foot. If window function W has the minimum value, subject 2 has the center of gravity on the right foot. In other words, in FIG. 7, subject 2 has left foot axis L in a walking time when window function W has the maximum value. Subject 2 has right foot axis R in a walking time when window function W has the minimum value.

Window function W is not limited to a rectangular window function shown in FIG. 7. A Hanning window function or the like may be used instead. Alternatively, window function W may be periodically replaced with another window function. For example, window function W may be an identical window function every three periods (the period of six steps in total, including three times of the right foot axis and three times of the left foot axis in total), only the first and last steps in the three periods may have Hanning window functions, and two periods (four steps) between the first and last steps may be weighted as rectangular window functions.

In FIG. 7, window function W is set such that subject 2 has left foot axis L in a walking time when window function W has the maximum value and subject 2 has right foot axis R in a walking time when window function W has the minimum value. The setting of window function W is not limited. Window function W may be set such that subject 2 has right foot axis R in a walking time when window function W has the maximum value and subject 2 has left foot axis L in a walking time when window function W has the minimum value.

Moreover, in FIG. 7, window function W is calculated using the acceleration data in X-axis direction. The acceleration data is not limited. Window function W may be calculated using the acceleration data in Y-axis direction.

Figure 8:
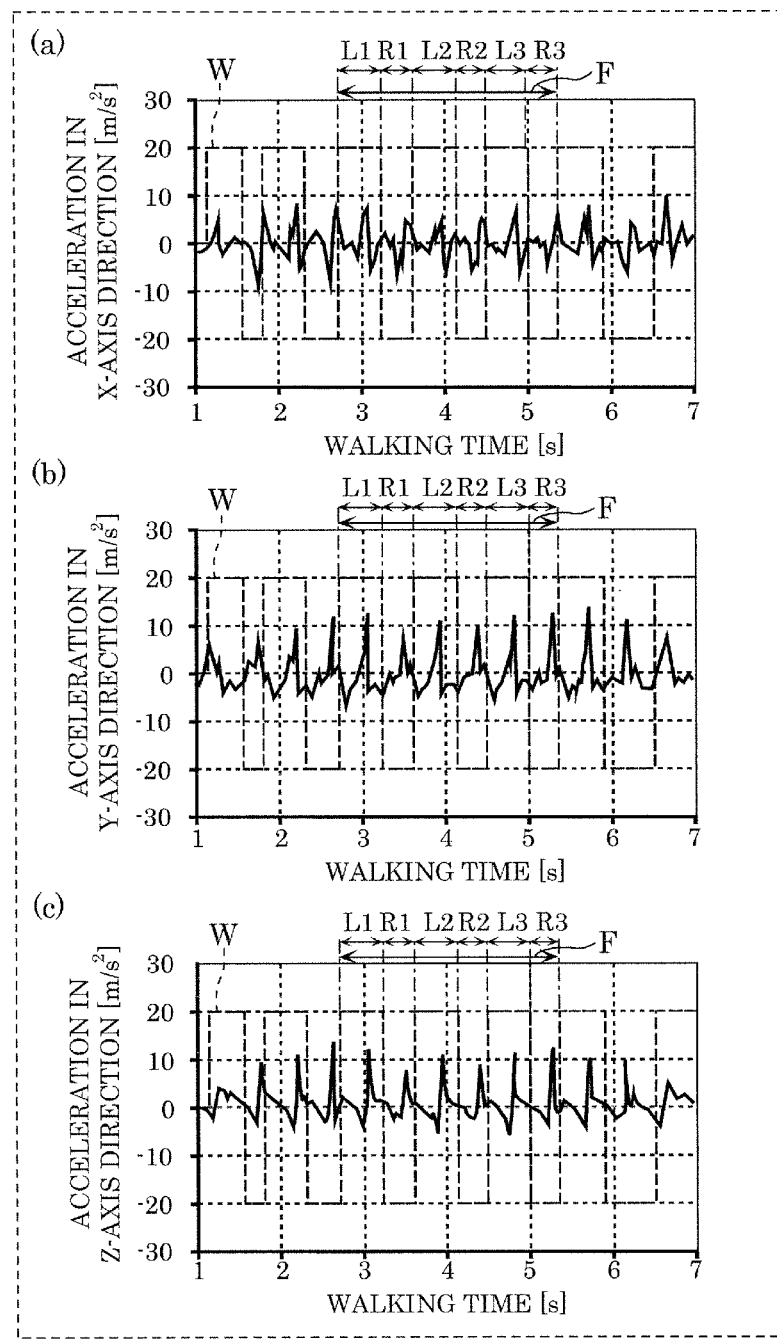
FIG. 8 shows the acceleration data acquired by the cognitive function evaluation device according to Embodiment 1 and the window function calculated by the cognitive function evaluation device according to Embodiment 1.

FIG. 8 shows window function W and the acceleration data measured by cognitive function evaluation device 100 according to Embodiment 1. Specifically, FIG. 8 shows that window function W calculated by calculating unit 103 is superimposed on the acceleration data in FIG. 5. Window function W is superimposed on the acceleration data according to a walking time on the horizontal axis of FIG. 8. The maximum value and the minimum value of window function W are optionally multiplied by a constant for the sake of explanation. FIG. 8(*a*) shows that window function W is superimposed on the acceleration data in FIG. 5(*a*). FIG. 8(*b*) shows that window function W is superimposed on the acceleration data in FIG. 5(b). FIG. 8(c) shows that window function W is superimposed on the acceleration data in FIG. 5(c).

As shown in FIG. 8, calculating unit 103 determines, in real time, a time period F (Fourier transform range F), which is the range of a walking time for Fourier transform on the acceleration data, from the acceleration data and window function W. In many cases, the acceleration data is not stabilized when subject 2 starts walking (for example, the walking time of about 0 to 2 seconds). Thus, Fourier transform range F is not particularly limited but is preferably a walking time several seconds after subject 2 starts walking. In Embodiment 1, Fourier transform range F is started when subject 2 has left foot axis L1, that is, about 2.7 seconds after subject 2 starts walking. In Embodiment 1, Fourier transform range F is ended when subject 2 has right foot axis R3, that is, about 5.3 seconds after subject 2 starts walking. In other words, in Embodiment 1, calculating unit 103 determines, as Fourier transform range F, the walking time of a range where subject 2 takes six steps in total, the steps including three steps on left foot axes L1, L2, and L3 and three steps on right foot axes R1, R2, and R3. Specifically, calculating unit 103 determines, as Fourier transform range F, a walking time when the foot axis changes to left foot axis L1, right foot axis R1, left foot axis L2, right foot axis R2, left foot axis L3, and then right foot axis R3 in the walking time of subject 2.

Fourier transform range F is the sum of steps of subject 2 on right foot axis R and left foot axis L while walking, that is, the walking time of the sum of steps. The sum of steps is not limited. The sum of steps may be, for example, six or eight.

Moreover, Fourier transform range F is set so as to totally include a walking time in the state of right foot axis R for each step or the state of left foot axis L for each step.

Fourier transform is not limited and may be discrete Fourier transform (DFT) or fast Fourier transform (FFT). In Embodiment 1, Fourier transform performed by calculating unit 103 is DFT.

Figure 9A:
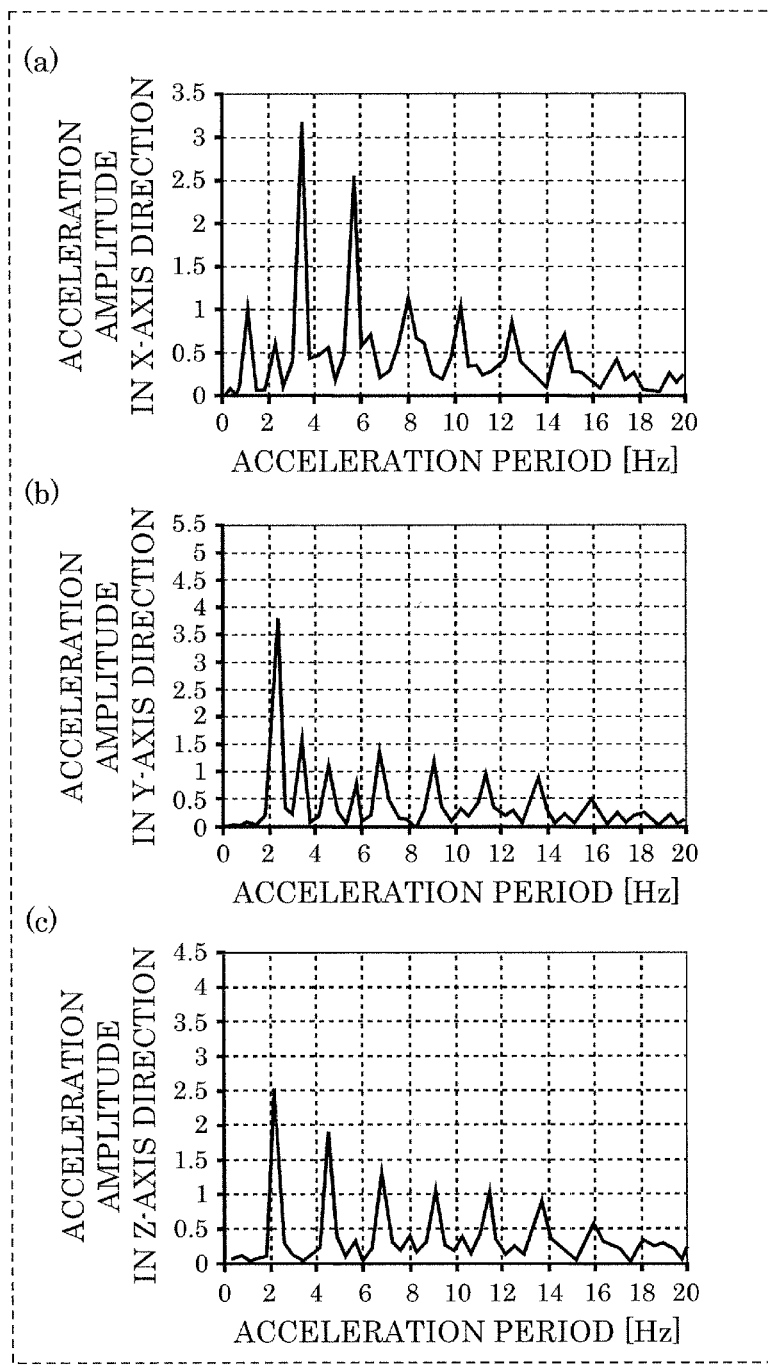
FIG. 9A shows data calculated by Fourier transform performed on the acceleration data by the cognitive function evaluation device according to Embodiment 1.

FIG. 9A shows a spectrum (frequency spectrum) calculated by Fourier transform performed on the acceleration data by cognitive function evaluation device 100 according to Embodiment 1. Specifically, FIG. 9A shows data obtained by performing DFT on the acceleration data by calculating unit 103 in Fourier transform range F shown in FIG. 8. FIG. 9A(a) shows data obtained by performing DFT on the acceleration data in X-axis direction by calculating unit 103. FIG. 9A(b) shows data obtained by performing DFT on the acceleration data in Y-axis direction by calculating unit 103. FIG. 9A(c) shows data obtained by performing DFT on the acceleration data in Z-axis direction by calculating unit 103.

In this case, the absolute value of the amplitude of the frequency spectrum varies among subjects 2. In order to compare the frequency spectra of subjects, the frequency spectra are standardized with low frequency components from about 0 to 6 Hz and at a frequency (dominant frequency) having peak intensity (large amplitude).

Figure 9B:
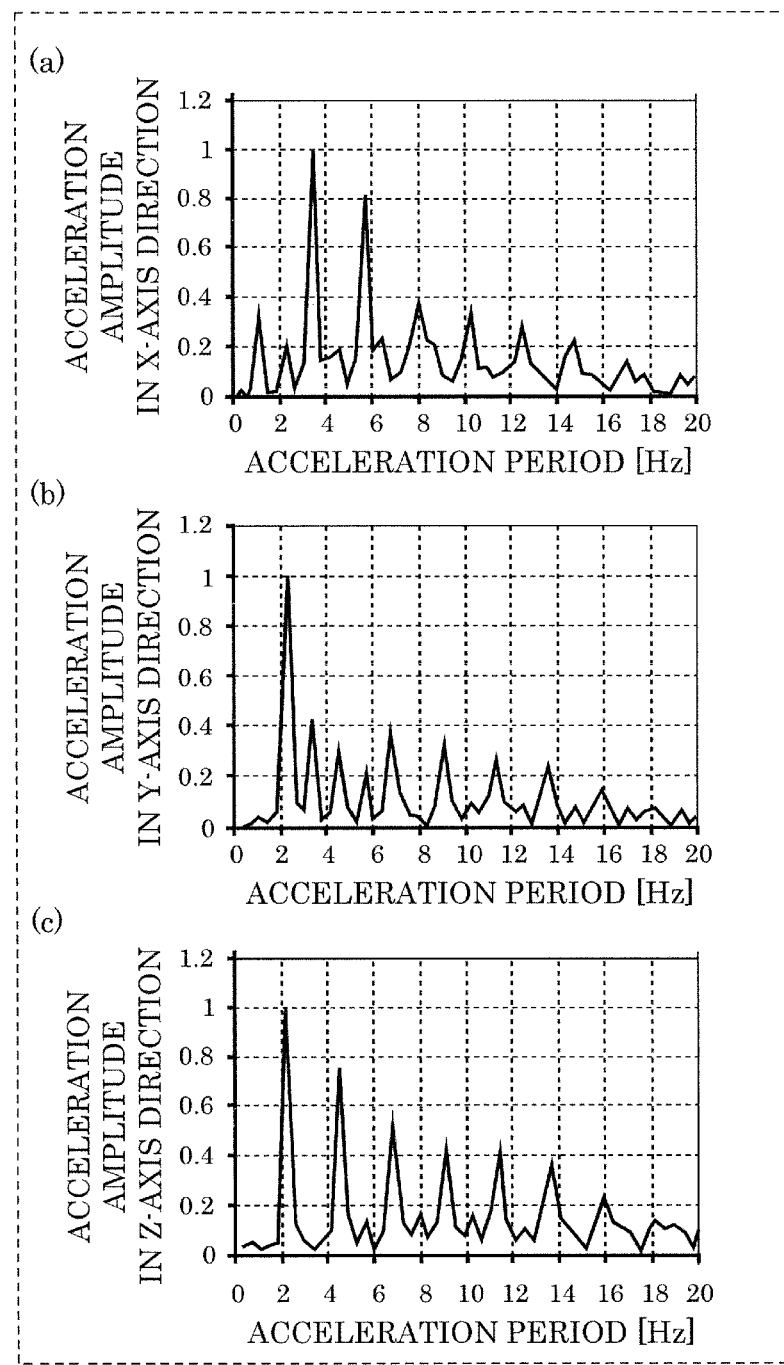
FIG. 9B shows data obtained by standardizing the data in FIG. 9A.

FIG. 9B shows data obtained by standardizing the frequency spectrum in FIG. 9A by the amplitude (acceleration amplitude) of the dominant frequency. FIG. 9B(a) shows data obtained by standardizing the frequency spectrum in X-axis direction by calculating unit 103. FIG. 9B(b) shows data obtained by standardizing the frequency spectrum in Y-axis direction by calculating unit 103. FIG. 9B(c) shows data obtained by standardizing the frequency spectrum in Z-axis direction by calculating unit 103.

As shown in FIGS. 9A and 9B, the larger the acceleration period (frequency) is, the smaller the amplitude is. In other words, low-frequency components from about 0 to 6 Hz have a large amplitude, whereas high-frequency components at 6 Hz or higher have a smaller amplitude than the low-frequency components.

The amplitude of the low-frequency components is regarded as an amplitude generated by moving the center of gravity between the right foot and the left foot of subject 2 walking. The amplitude of the high-frequency components is regarded as an amplitude generated by an involuntary movement (unintentional movement) of subject 2 in a lateral direction (X-axis direction) while walking. Specifically, it is considered that a dementia patient who declines in brain function or muscle strength has stronger (more frequent) orthostatic tremors (uncontrollable rhythmic movements when the patient stands up) at 6 to 20 Hz than a person in good health in order to laterally keep balance while walking. In other words, it is considered that the characteristics of dementia are reflected particularly on high-frequency components at 6 Hz or higher among the frequency spectra.

In Embodiment 1, the periodicity of a body movement of subject 2 walking is frequency components at a higher frequency than a walking frequency among frequency components constitutes the body movement of subject 2, the periodicity being calculated by calculating unit 103. Specifically, in Embodiment 1, data indicating the periodicity of a body movement is data on high-frequency components in the frequency spectrum.

In this case, in Embodiment 1, calculating unit 103 calculates the integral of high-frequency components among the standardized frequency spectra (i.e., data in FIG. 9B). Specifically, in Embodiment 1, calculating unit 103 calculates the integral of the standardized frequency spectra of high-frequency components at 6 Hz to 20 Hz.

FIG. 10 is a flowchart showing the steps of calculating the integral of an example from the acceleration data by cognitive function evaluation device 100 according to Embodiment 1. Specifically, the flowchart shows the steps of calculating the integral of an example from the acceleration data by calculating unit 103. In FIG. 10, substantially the same steps as those of the flowchart of FIG. 6 are indicated by the same reference numerals and the explanation of the steps may be omitted or simplified.

As shown in FIG. 10, calculating unit 103 acquires, in real time, the acceleration data stored in storing unit 102 (step S10). Subsequently, calculating unit 103 calculates window function W from the acquired acceleration data (step S11). Specifically, calculating unit 103 calculates window function W in steps S101 to S106 in FIG. 6. Calculating unit 103 then determines Fourier transform range F from the calculated window function W (step S12). Thereafter, calculating unit 103 performs Fourier transform on the acceleration data according to Fourier transform range F (step S13). Specifically, in step S13, calculating unit 103 calculates the frequency spectrum from the acceleration data, the frequency spectrum indicating the periodicity of the body movement of subject 2 walking. Calculating unit 103 then standardizes the calculated frequency spectrum with the amplitude of a frequency having the peak intensity (step S14). Subsequently, calculating unit 103 calculates an integral by integrating the high-frequency components of the standardized frequency spectrum (step S15). In Embodiment 1, the high-frequency components are set at 6 Hz to 20 Hz. The upper limit of a high-frequency domain is not particularly limited and may be 30 Hz or 50 Hz. According to embodiments, the calculating unit 103 operates with a sampling frequency (or Nyquist rate) of around 100 Hz.

Thus, calculating unit 103 calculates the integral of subject 2 from the acceleration data.

In the diagnosis of dementia, subject 2 undergoes a MoCA, that is, a batch test for the diagnosis of dementia, thereby determining whether subject 2 has dementia or not. FIG. 11 shows scores obtained when MoCA tests were conducted on subjects 2.

As shown in FIG. 11, the inventors conducted MoCA tests on a plurality of subjects including persons in good health (NC: Normal Controls), patients with mild dementia (MCI: Mild Cognitive Impairment), and dementia patients (AD). The number of subjects was 90, the number of MCI subjects was 94, and the number of AD subjects was 93.

As shown in FIG. 11, it can be confirmed that NC, MCI, and AD have different MoCA average scores and MoCA score ranges. Specifically, the MoCA average score of NC is 27.4, the MoCA average score of MCI is 22.1, and the MoCA average score of AD is 16.2.

Figure 12:
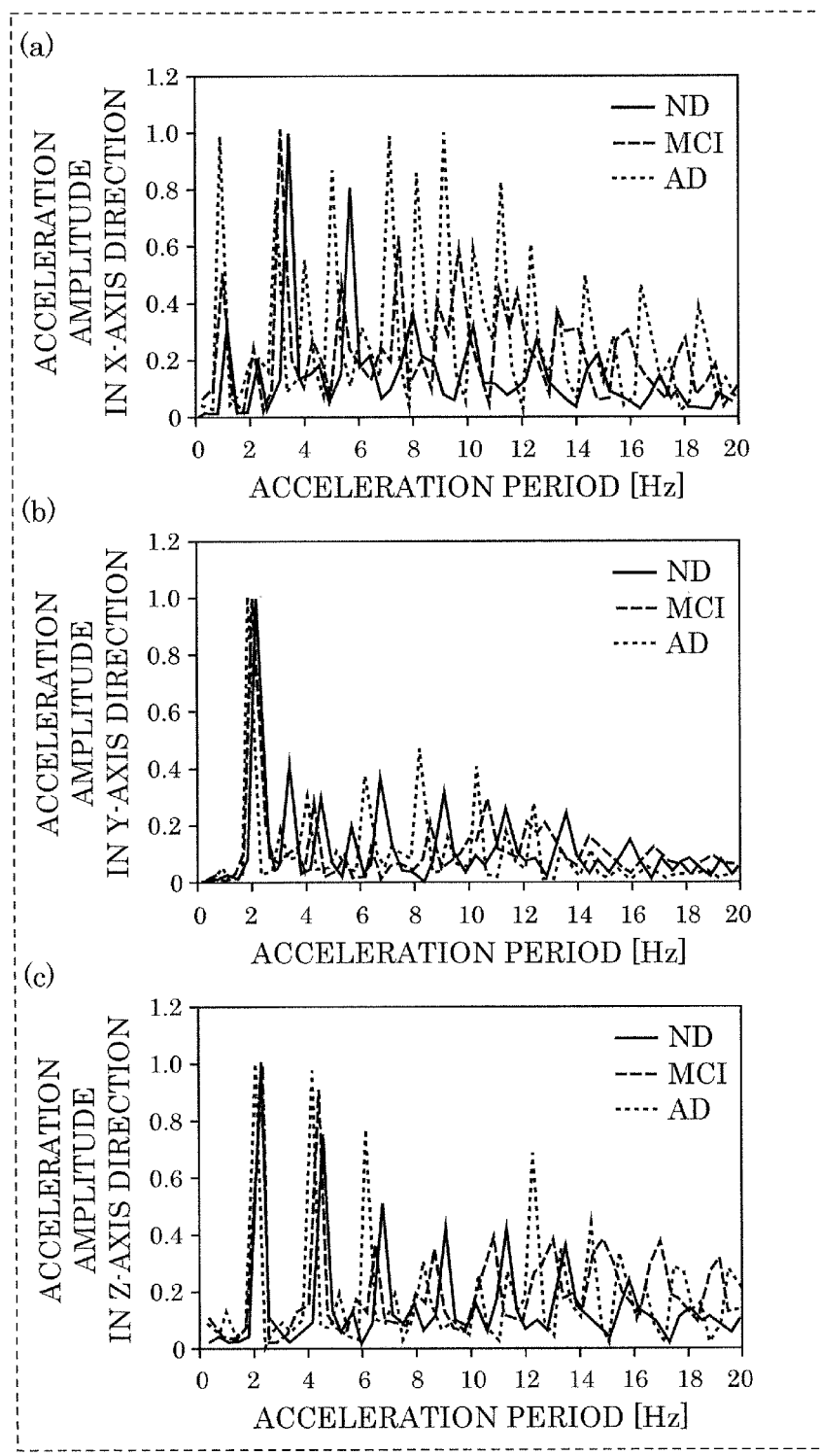
FIG. 12 shows a specific example of frequency spectra calculated from the acceleration data on persons in good health, patients with mild dementia, and dementia patients who are measured by a body movement sensor.

FIG. 12 shows a specific example of frequency spectra calculated from the acceleration data on ND, MCI, and AD that are measured by body movement sensor 105. Specifically, FIG. 12 shows the frequency spectra calculated from the acceleration data on ND, MCI, and AD who walk in the negative direction along Z axis. Each of ND, MCI, and AD identified by MoCA tests wears attachment 11 as illustrated in FIG. 3. In FIG. 12, the vertical axis of the acceleration data indicates an acceleration amplitude and the horizontal axis of the acceleration data indicates an acceleration period. FIG. 12(a) shows the frequency spectra of ND, MCI, and AD in X-axis direction. FIG. 12(b) shows the frequency spectra of ND, MCI, and AD in Y-axis direction. FIG. 12(c) shows the frequency spectra of ND, MCI, and AD in Z-axis direction.

As shown in FIG. 12(a), it is understood that MCI and AD have higher peak intensity than ND at the high-frequency components of 6 Hz or higher. Specifically, it is understood that MCI and AD have a larger acceleration amplitude than ND at 6 Hz or higher. The inventors found that the integral obtained by integrating the high-frequency components of frequency spectra calculated from the acceleration data is applied as a value for identifying the cognitive function level.

Figure 13:
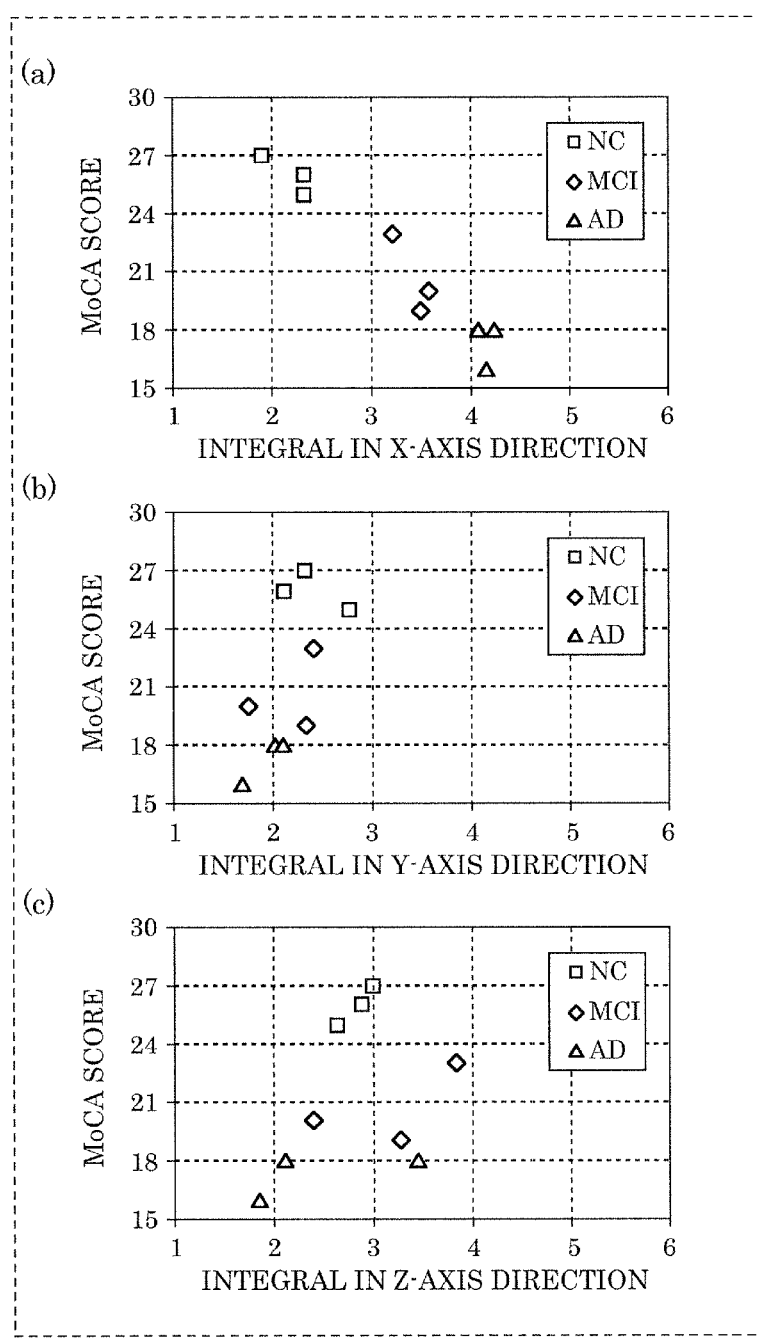
FIG. 13 shows scores obtained by the subjects in MoCA tests relative to the integrals of the subjects, the integrals being calculated by the cognitive function evaluation device according to Embodiment 1.

FIG. 13 shows scores obtained by the subjects in MoCA tests relative to the integrals of the subjects according to the example, the integrals being calculated by cognitive function evaluation device 100 according to Embodiment 1. The inventors extracted three subjects for each of NC, MCI, and AD from the subjects having undergone the MoCA tests. Moreover, the inventors acquired body movement data (specifically, acceleration data) on walking by means of cognitive function evaluation device 100 and obtained data (specifically, the integrals) on the periodicity of body movements from the body movement data. FIG. 13(a) shows MoCA test scores relative to the integrals at 6 Hz or higher in the frequency spectrum in X-axis direction. FIG. 13(b) shows MoCA test scores relative to the integrals at 6 Hz or higher in the frequency spectrum in Y-axis direction. FIG. 13(c) shows MoCA test scores relative to the integrals at 6 Hz or higher in the frequency spectrum in Z-axis direction.

As shown in FIG. 13(a), the correlation between the integral in X-axis direction and the MoCA test score varies among NC, MCI, and AD. Specifically, ND in X-axis direction has an integral of 2.5 or smaller, MCI in X-axis direction has an integral of 3.0 to 3.8, and AD in X-axis direction has an integral of 4.0 or larger. In other words, one of NC, MCI, and AD can be identified based on the integral calculated from the acceleration data.

The integrals and reference data 110 on correlations with ND, MCI, and AD are stored in storing unit 102 provided in cognitive function evaluation device 100. Calculating unit 103 calculates the integral, that is, data on the periodicity of a body movement from the body movement data (e.g., the acceleration data) acquired by acquiring unit 101 and identifies the cognitive function level of subject 2 by comparing the calculated integral and reference data 110.

NC, MCI, and AD are difficult to distinguish from one another from the MoCA test scores relative to the integrals in Y-axis direction and Z-axis direction shown in FIGS. 13(b) and 13(c). However, regarding the integrals in Y-axis direction and Z-axis direction, NC, MCI, and AD may be made distinguishable from one another as shown in FIG. 13(a) by increasing the measurement results of subject 2.

Figure 14:
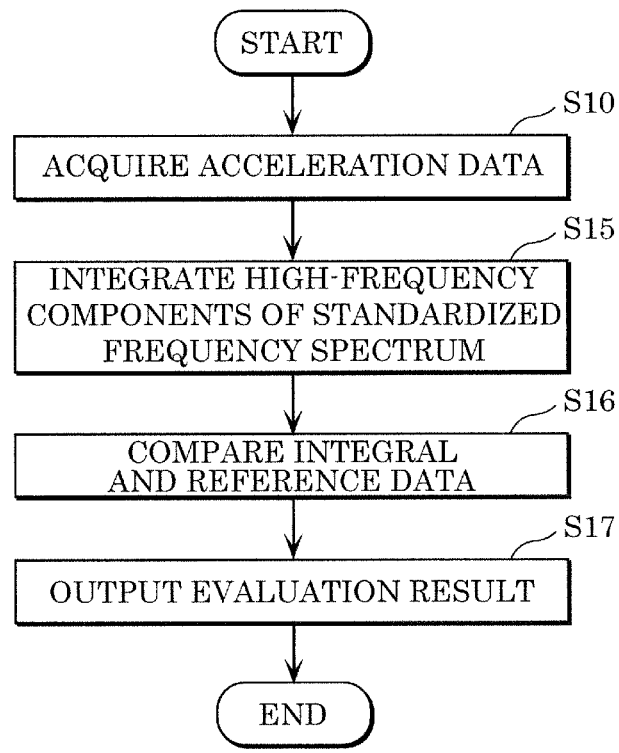
FIG. 14 is a flowchart showing the steps of identifying the cognitive function level from the acceleration data acquired by the cognitive function evaluation device according to Embodiment 1.

FIG. 14 is a flowchart showing the steps of identifying the cognitive function level from the body movement data measured by cognitive function evaluation device 100 according to Embodiment 1. Specifically, FIG. 14 is a flowchart showing the steps of identifying the cognitive function level of subject 2 by calculating unit 103 from the body movement data of subject 2 walking.

As shown in FIG. 14, acquiring unit 101 acquires the acceleration data measured by acceleration sensor 10 (step S10). Subsequently, calculating unit 103 calculates the standardized frequency spectrum from the acceleration data and calculates the integral of the high-frequency components of the frequency spectrum (step S15). Specifically, calculating unit 103 calculates the integral by performing S10 to S15 shown in FIG. 10. Subsequently, calculating unit 103 identifies the cognitive function level of subject 2 by checking the calculated integral against reference data 110 stored in advance in storing unit 102 (step S16). Calculating unit 103 then controls indicating unit 104 so as to display the evaluation result of the identified cognitive function level (step S17). For example, if the cognitive function level of subject 2 is identified as MCI by calculating unit 103, calculating unit 103 may control indicating unit 104 so as to display an image generated to indicate the possibility of MCI. Thus, cognitive function evaluation device 100 can easily identify the cognitive function level of subject 2.

[Effects]

As described above, cognitive function evaluation device 100 of Embodiment 1 includes storing unit 102 that stores reference data on the relationship between the periodicity of a body movement of a person walking and the cognitive function level of the person. Moreover, cognitive function evaluation device 100 includes acquiring unit 101 that acquires body movement data on a detected body movement from body movement sensor 105 that detects a body movement of subject 2 walking. Cognitive function evaluation device 100 further includes calculating unit 103 that calculates the periodicity of a body movement from the acquired body movement data and checks the calculated periodicity of the body movement against the reference data stored in storing unit 102. Calculating unit 103 identifies the cognitive function level corresponding to the calculated periodicity of the body movement.

Thus, cognitive function evaluation device 100 can identify the cognitive function level of subject 2 without the need for a time for the MoCA test. In other words, cognitive function evaluation device 100 can quickly identify the cognitive function level of subject 2. Furthermore, cognitive function evaluation device 100 can easily identify the cognitive function level of subject 2, thereby identifying cognitive function levels with high frequency. Thus, cognitive function evaluation device 100 allows subject 2 to easily confirm the temporal change in the cognitive function of subject 2.

The periodicity of a body movement is frequency components at a higher frequency than a frequency for walking among frequency components constituting the body movement.

In other words, calculating unit 103 calculates the high-frequency components having different frequency spectrum characteristics for ND, MCI, and AD, as the characteristics of the periodicity of the body movement. Thus, cognitive function evaluation device 100 can accurately identify the cognitive function level of subject 2.

The body movement data may be data that indicates a change in the body movement over time. Moreover, calculating unit 103 may calculate a frequency spectrum by analyzing frequency of the body movement data and calculate, as the periodicity of a body movement, an integral at a higher frequency than a frequency for walking in the calculated frequency spectrum.

This allows cognitive function evaluation device 100 to calculate the periodicity of the body movement from data further varying in characteristics among ND, MCI, and AD. Thus, cognitive function evaluation device 100 can more accurately identify the cognitive function level of subject 2.

The body movement data may be data that indicates a change in the acceleration of the body movement over time. Moreover, calculating unit 103 may identify time period F, during which subject 2 makes a predetermined number of steps while walking, from the body movement data and perform frequency analysis on the body movement data in the identified time period F.

This allows cognitive function evaluation device 100 to calculate the periodicity of the body movement while removing disruption of the body movement data particularly at the start of walking. Thus, cognitive function evaluation device 100 can more accurately identify the cognitive function level of subject 2.

The body movement data may be data that indicates a change in the acceleration of subject 2 over time in a horizontal direction orthogonal to the walking direction in which subject 2 is walking.

Specifically, the body movement data may be data that indicates a change in the acceleration of subject 2 over time in X-axis direction if subject 2 walks in the negative direction of Z axis as illustrated in FIG. 3. Thus, cognitive function evaluation device 100 can more accurately identify the cognitive function level of subject 2.

A cognitive function evaluation method according to Embodiment 1 includes the step of acquiring body movement data indicating a detected body movement from body movement sensor 105 that detects the body movement of subject 2 walking, and the step of calculation. In the step of calculation, the periodicity of the body movement is calculated from the acquired body movement data. Moreover, in the step of calculation, the calculated periodicity of the body movement is checked against reference data 110 that is stored in storing unit 102 and indicates the relationship between the periodicity of a body movement of a person walking and the cognitive function of the person, thereby identifying the cognitive function level corresponding to the calculated periodicity of the body movement.

Thus, the cognitive function evaluation method can evaluate the cognitive function level of subject 2 without the need for a time for the MoCA test. In other words, the cognitive function evaluation method can quickly identify the cognitive function level of subject 2. Furthermore, the cognitive function evaluation method can easily identify the cognitive function level of subject 2, thereby identifying cognitive function levels with high frequency. Thus, the cognitive function evaluation method allows subject 2 to easily confirm the temporal change in the cognitive function of subject 2.

The present invention may be implemented as a non-transitory computer-readable recording medium having recorded thereon a program that causes a computer to perform the steps included in the cognitive function evaluation method.

Thus, the cognitive function evaluation method can be implemented by a computer as a program that can easily evaluate the cognitive function of subject 2.

Embodiment 2

A cognitive function evaluation device according to Embodiment 2 will be described below.

In Embodiment 1, calculating unit 103 integrates the high-frequency components of the body movement data (acceleration data) having undergone Fourier transform, so that an integral is obtained as data on the periodicity of a body movement of subject 2 walking. In Embodiment 2, the step length of subject 2 or a time for each step (the time of a step) from body movement data is calculated as data indicating the periodicity of a body movement of subject 2.

A cognitive function evaluation device according to Embodiment 2 will be described below. Substantially the same configurations or the same operations as Embodiment 1 are indicated by the same reference numerals and the redundant explanation thereof may be omitted or simplified.

[The Configuration of the Cognitive Function Evaluation Device]

Figure 15:
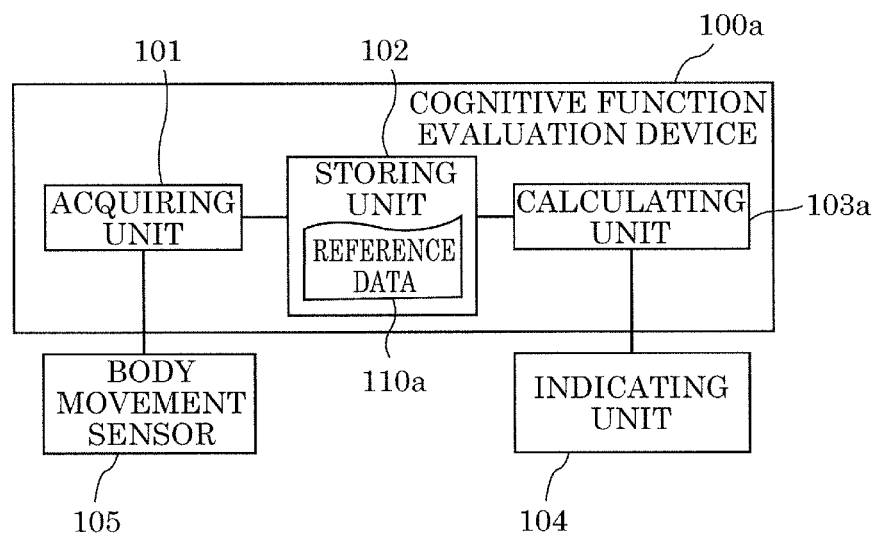
FIG. 15 is a block diagram illustrating the characteristic functional configuration of a cognitive function evaluation device according to Embodiment 2.

FIG. 15 is a block diagram illustrating the characteristic functional configuration of cognitive function evaluation device 100a according to Embodiment 2. As illustrated in FIG. 15, cognitive function evaluation device 100a includes acquiring unit 101, storing unit 102, and calculating unit 103a.

As in Embodiment 1, acquiring unit 101 is a processing unit that acquires body movement data on a subject measured by body movement sensor 105. Acquiring unit 101 is implemented by, for example, a CPU, control programs stored in storing unit 102, and a communication interface.

As in Embodiment 1, storing unit 102 is memory that stores the body movement data acquired by acquiring unit 101. Storing unit 102 includes, for example, ROM, RAM, or an HDD. Moreover, storing unit 102 stores reference data 110a to be checked by calculating unit 103 against the periodicity of a body movement calculated from the body movement data acquired by acquiring unit 101. Reference data 110a will be specifically discussed later.

As in Embodiment 1, calculating unit 103a is a processing unit that calculates the periodicity of a body movement from the body movement data acquired by acquiring unit 101. Calculating unit 103 is implemented by, for example, a CPU and control programs stored in storing unit 102.

In this configuration, calculating unit 103a is different from calculating unit 103 of Embodiment 1 in the method of calculating the periodicity of a body movement from the acquired body movement data. Specifically, the step length of subject 2 or the time of a step obtained from the acquired body movement data is calculated as data indicating the periodicity of a body movement of subject 2.

Example

Figure 16A:
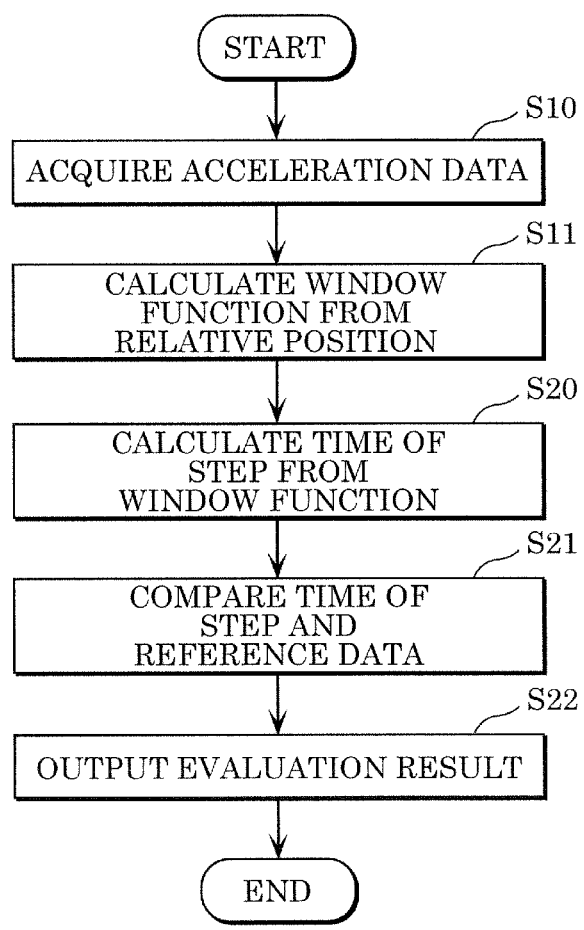
FIG. 16A is a flowchart showing the steps of calculating the time of a step from the acceleration data by the cognitive function evaluation device according to Embodiment 2.
Figure 16B:
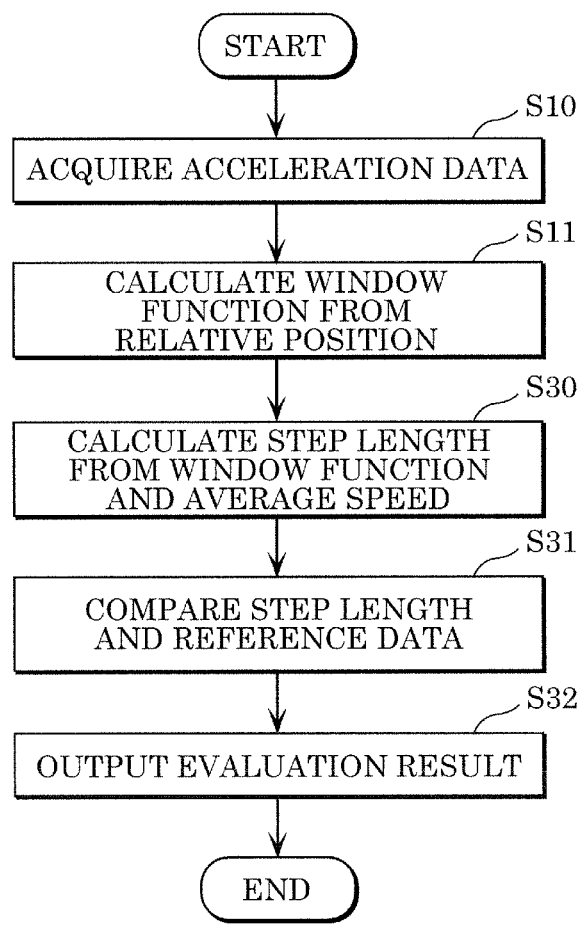
FIG. 16B is a flowchart showing the steps of calculating a step length from the acceleration data by the cognitive function evaluation device according to Embodiment 2.

FIG. 16A is a flowchart showing the steps of calculating the time of a step from acceleration data by cognitive function evaluation device 100a according to Embodiment 2. FIG. 16B is a flowchart showing the steps of calculating a step length from the acceleration data by cognitive function evaluation device 100a according to Embodiment 2.

In Embodiment 2, body movement sensor 105 is an acceleration sensor (triaxial acceleration sensor) as in Embodiment 1. Attachment 11 in FIG. 3 is attached to subject 2 so as to acquire acceleration data on subject 2.

As shown in FIGS. 16A and 16B, calculating unit 103a acquires the acceleration data stored in storing unit 102 (step S10). Subsequently, calculating unit 103a calculates window function W from the acquired acceleration data (step S11). Specifically, these steps are similar to those of the flowchart of FIG. 6. Calculating unit 103a calculates a speed by integrating the acquired acceleration data (step S101). Calculating unit 103a then calculates the average speed of subject 2 from the calculated speed (step S102). At this point, calculating unit 103 calculates a relative speed by determining a difference between the calculated speed and the calculated average speed (step S103). Calculating unit 103 then calculates the position of subject 2 by integrating the calculated relative speed (step S104). Subsequently, calculating unit 103a calculates an average relative position from the calculated position of subject 2 (step S105). At this point, calculating unit 103a calculates a relative position by determining a difference between the calculated position of subject 2 and the calculated average relative position (step S106). Calculating unit 103a then calculates window function W from the calculated relative position (step S11). Calculating unit 103a then calculates the time of a step from calculated window function W (step S20). Specifically, window function W is calculated from the acceleration data, thereby calculating the same data as the relative position data in FIG. 7.

As described above, window function W is a function calculated from relative position data on subject 2 relative to a walking time. The function indicates whether the center of gravity is located on the right foot or the left foot of subject 2 walking. Specifically, the position of the center of gravity in a predetermined walking time of subject 2 can be easily estimated from a walking time when window function W has the maximum value or the minimum value. Specifically, as shown in FIG. 7, subject 2 has the center of gravity on the left foot (left foot axes L1, L2, and L3) when the window function W has the maximum value. When window function W has the minimum value, subject 2 has the center of gravity on the right foot (right foot axes R1, R2, and R3).

Thus, a walking time in the state of left foot axis L or the state of right foot axis R for each step in FIG. 7 is the time of a step of subject 2. In other words, calculating unit 103a calculates the time of a step from the walking time of left foot axis L or right foot axis R for each step.

As shown in FIG. 16B, calculating unit 103a calculates the step length of subject 2 from calculated window function W (step S30). Specifically, window function W is calculated from the acceleration data, thereby calculating the same data as relative position data on subject 2 with respect to the walking time shown in FIG. 7. Moreover, the length of a step (step length) can be calculated by a multiplication of the time of the step and the average speed calculated from step S102 of FIG. 6. In other words, calculating unit 103a calculates the step length from the time of a step of subject 2 and the average speed of subject 2.

Furthermore, a data point (or a data range) used for calculating the time of a step and a step length from window function W is not limited. For example, data is unstable when subject 2 starts walking (for example, the walking time of about 0 to 2 seconds). Thus, in order to calculate the time of a step and a step length, data may be used several seconds after subject 2 starts walking. Alternatively, when the time of a step and a step length are calculated, calculating unit 103a may calculate the time of a step and a step length from the average value of data on several steps (e.g., six steps).

Figure 17:
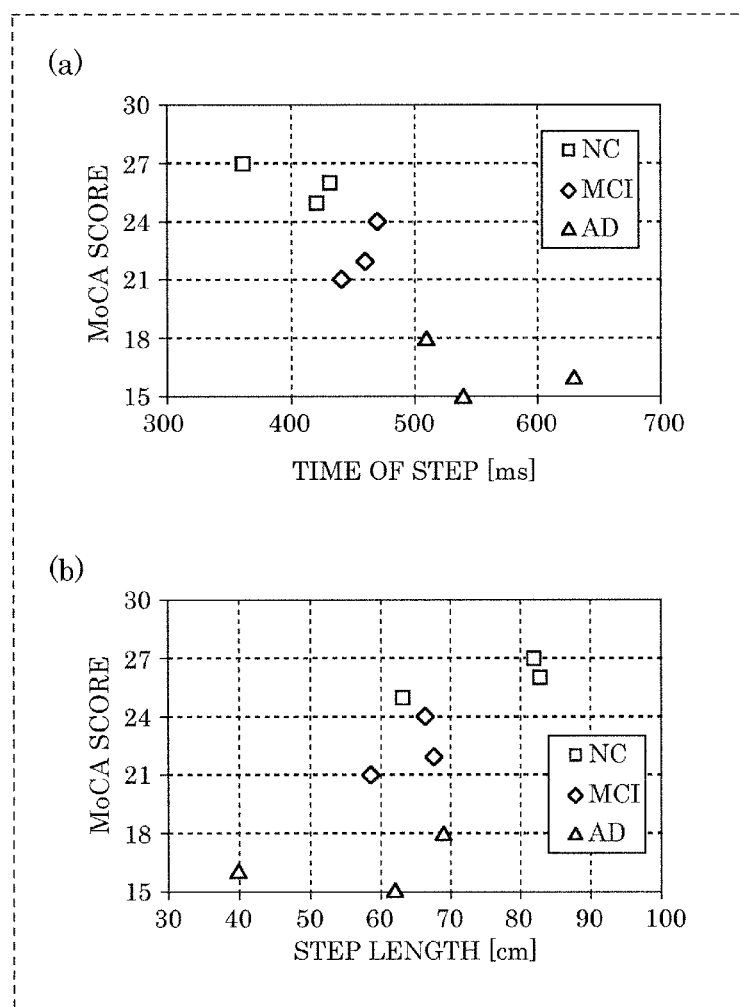
FIG. 17 shows an example of scores obtained by the subjects in MoCA tests with respect to the time of a step and a step length of each subject, the time and step being calculated by the cognitive function evaluation device according to Embodiment 2.

FIG. 17 shows scores obtained by the subjects in MoCA tests with respect to the time of a step and a step length of each subject measured by cognitive function evaluation device 100a according to Embodiment 2. Specifically, as in Embodiment 1, the inventors extracted three subjects for each of NC, MCI, and AD from the subjects having undergone the MoCA tests. The inventors then acquired body movement data (specifically, acceleration data) from the extracted subjects by means of cognitive function evaluation device 100a and obtained the time of a step and a step length from the acceleration data. In other words, FIG. 17 shows MoCA test scores with respect to the time of a step and a step length of each subject. FIG. 17(a) shows a MoCA test score with respect to the time of a step of subject 2. FIG. 17(b) shows a MoCA test score with respect to the step length of subject 2.

As shown in FIG. 17(a), the correlation between the time of a step and the MoCA test score varies among NC, MCI, and AD. Specifically, the time of a step of ND is less than 425 ms, the time of a step of MCI is 425 ms to less than 500 ms, and the time of a step of AD is at least 500 ms. In other words, one of NC, MCI, and AD can be identified based on the time of step that is a converted value of the acceleration data.

The time of a step or a step length and reference data 110 on correlations with ND, MCI, and AD are stored in advance in storing unit 102 provided in cognitive function evaluation device 100a. Calculating unit 103a calculates the time of a step or a step length from the body movement data (e.g., the acceleration data) acquired by acquiring unit 101 and identifies the cognitive function level of subject 2 by comparing the calculated time of step or step length and reference data 110a. In short, in Embodiment 2, the periodicity of a body movement is the time of a step or a step length during walking. Specifically, in Embodiment 2, data on the periodicity of a body movement is a time for each step or a step length of subject 2 walking.

As shown in FIG. 16A, calculating unit 103a compares the time of a step and reference data 110a, the time being calculated in step S20 (step S21). Specifically, calculating unit 103a identifies the cognitive function level of subject 2 by checking the time of a step against reference data 110a stored in storing unit 102. Calculating unit 103a then outputs an evaluation result indicating the identified cognitive function level (step S22).

As shown in FIG. 16B, calculating unit 103a compares the step length calculated in step S30 and reference data 110a (step S21). Specifically, calculating unit 103a identifies the cognitive function level of subject 2 by checking the step length against reference data 110a stored in storing unit 102. Calculating unit 103a then outputs an evaluation result indicating the identified cognitive function level (step S32).

For example, if the cognitive function level of subject 2 is identified as MCI by calculating unit 103a in steps S22 and S32, calculating unit 103 may control indicating unit 104 so as to display an image generated to indicate the possibility of MCI.

Thus, cognitive function evaluation device 100a can easily identify the cognitive function level of subject 2.

NC, MCI, and AD are difficult to distinguish from one another from the MoCA test scores relative to step lengths in FIG. 17(b). NC, MCI, and AD may be made distinguishable from one another as shown in FIG. 17(a) by increasing the measurement results of subject 2.

[Effects]

As described above, cognitive function evaluation device 100a according to Embodiment 2 includes storing unit 102 and acquiring unit 101 like cognitive function evaluation device 100 according to Embodiment 1. Cognitive function evaluation device 100a according to Embodiment 2 further includes calculating unit 103a. Calculating unit 103a identifies the cognitive function level corresponding to the calculated periodicity of a body movement. In this case, the periodicity of a body movement may be the step length of subject 2 walking. Specifically, data indicating the periodicity of a body movement of subject 2 may be the step length of subject 2 walking.

Thus, cognitive function evaluation device 100a can accurately identify the cognitive function level of subject 2.

The body movement data may be data on a change in the acceleration of the body movement over time. Moreover, calculating unit 103a may identify time period F, during which subject 2 makes a predetermined number of steps while walking, from the body movement data and calculate a step length from the body movement data in identified time period F.

This allows cognitive function evaluation device 100a to calculate the periodicity of the body movement while removing disruption of the body movement data particularly at the start of walking. Thus, cognitive function evaluation device 100a can more accurately identify the cognitive function level of subject 2.

Moreover, the periodicity of the body movement may be the time of a step of subject 2 walking. Specifically, data indicating the periodicity of a body movement of subject 2 may be the time of a step of subject 2 walking.

Thus, cognitive function evaluation device 100a can accurately identify the cognitive function level of subject 2.

The body movement data may be data on a change in the acceleration of the body movement over time. Moreover, calculating unit 103 may identify time period F, during which subject 2 makes a predetermined number of steps while walking, from the body movement data and calculate the time of a step from the body movement data in identified time period F.

This allows cognitive function evaluation device 100a to calculate the periodicity of the body movement while removing disruption of the body movement data particularly at the start of walking. Thus, cognitive function evaluation device 100a can more accurately identify the cognitive function level of subject 2.

Moreover, calculating unit 103a may generate relative position data, which indicates a displacement of the center of gravity position of subject 2, from the body movement data and identify time period F based on the generated relative position data.

Thus, cognitive function evaluation device 100a can accurately calculate the periodicity of a body movement. This allows cognitive function evaluation device 100a to more accurately identify the cognitive function level of subject 2.

Modifications of the Present Embodiment

Modification 1

As described above, in Embodiments 1 and 2, body movement sensor 105 is an acceleration sensor 10. Calculating units 103 and 103a calculate the periodicity of a body movement by using the acceleration data measured by acceleration sensor 10. However, body movement sensor 105 is not limited to acceleration sensor 10. Body movement sensor 105 may be any device, e.g., a camera as long as body movement data on subject 2 can be detected.

Figure 18:
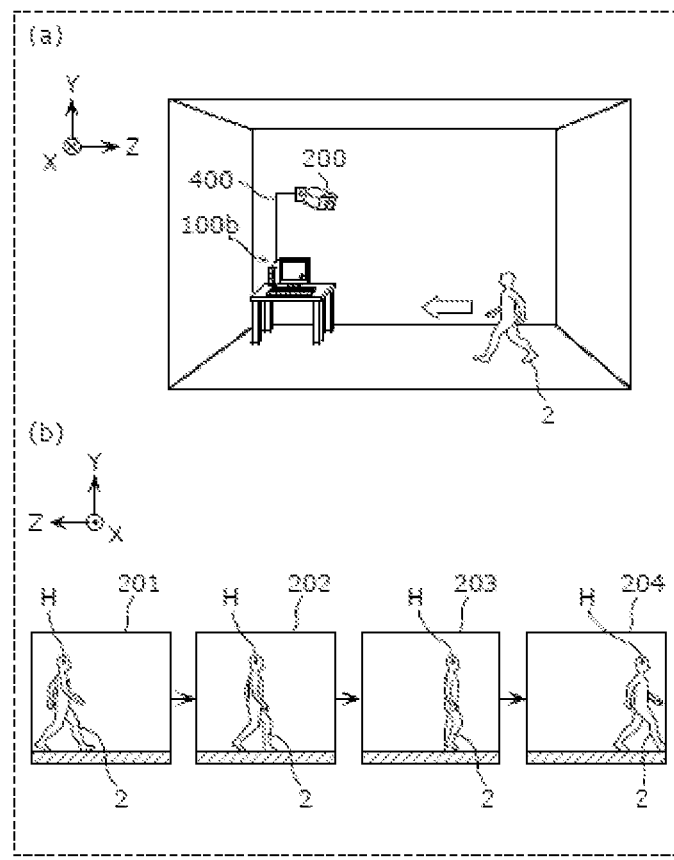
FIG. 18 illustrates a system configuration including a cognitive function evaluation device according to Modification 1 of the present embodiment.

FIG. 18 illustrates the system configuration of a cognitive function evaluation device according to Modification 1 of the present embodiment. In cognitive function evaluation device 100b according to Modification 1 of the present embodiment, body movement sensor 105 is camera 200. Camera 200 captures a moving image of subject 2, and then an acquiring unit acquires the moving image as body movement data. The characteristic functional configuration of cognitive function evaluation device 100b according to Modification 1 of the present embodiment is substantially identical to that of cognitive function evaluation device 100 of Embodiment 1 illustrated in FIG. 2. Modification 1 is different from Embodiment 1 in the kind of body movement sensor 105, the operation of the calculating unit, and the contents of reference data stored in storing unit 102.

FIG. 18(a) is a schematic diagram showing that an image of subject 2 is captured by camera 200.

As shown in FIG. 18(a), camera 200 captures a moving image of subject 2 from a fixed position on, for example, an interior wall during walking. Camera 200 is, for example, an image (or a moving image) pickup device including a CCD (Charge Coupled Device) image sensor or a CMOS (Complementary Metal Oxide Semiconductor) image sensor. Camera 200 is connected so as to be communicable with cognitive function evaluation device 100b via cable 400.

The calculating unit extracts, for example, a head, a shoulder, a hand, and a leg from the moving image captured by camera 200. FIG. 18(b) illustrates a specific example of the frames of a moving image captured by camera 200. Specifically, FIG. 18(b) illustrates a specific example of each frame of a moving image captured in the order of frame 201, frame 202, frame 203, and frame 204. In FIG. 18(b), the calculating unit extracts, for example, a head as recognized position H from the moving image captured by camera 200. Specifically, the calculating unit confirms the recognized position H in frames 201, 202, 203, and 204 so as to calculate the movement of recognized position H of subject 2 with respect to a walking time. This allows the calculating unit to calculate the periodicity of the body movement of subject 2 walking. For example, the calculating unit may calculate relative position data on subject 2 or calculate acceleration data on subject 2 according to a change in recognized position H in frames 201, 202, 203, and 204 with respect to a walking time. The calculating unit identifies the cognitive function level of subject 2 by checking data on the calculated periodicity of the body movement against reference data stored in storing unit 102 so as to correspond to the data on the periodicity.

In FIG. 18, camera 200 captures an image of subject 2 from the negative direction of X axis. Camera 200 does not always capture an image of subject 2 in this direction. Camera 200 may capture an image of subject 2 in Y-axis direction or Z-axis direction. For example, camera 200 is preferably installed so as to capture an image of subject 2 in Z-axis direction. Alternatively, camera 200 may include multiple cameras installed to measure the periodicity of walking of subject 2 in X-axis direction, Y-axis direction, and Z-axis direction.

Modification 2

As described above, in cognitive function evaluation device 100b according to Modification 1 of the present embodiment, an image (moving image) corresponding to a walking time is acquired as body movement data by using camera 200, which is a specific example of body movement sensor 105, and the cognitive function level of subject 2 is identified. In cognitive function evaluation device 100c according to Modification 2 of the present embodiment, body movement data is acquired by using a radio wave sensor as body movement sensor 105.

Figure 19:
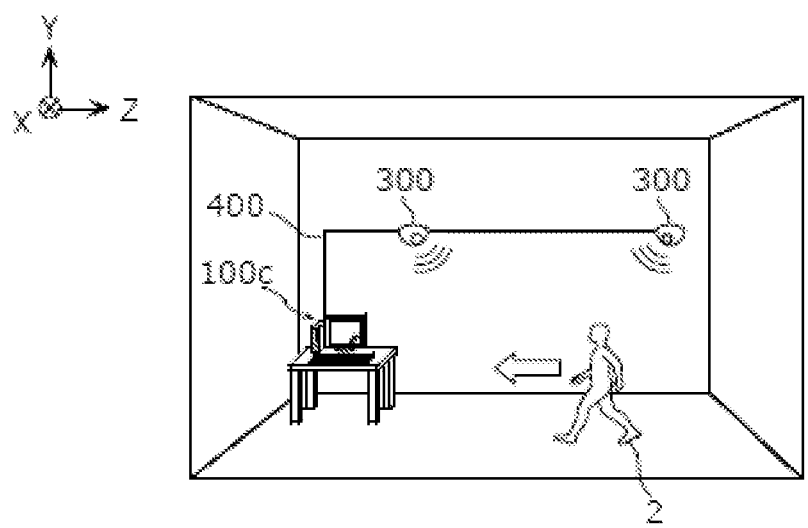
FIG. 19 illustrates a system configuration including a cognitive function evaluation device according to Modification 2 of the present embodiment.

FIG. 19 illustrates a system configuration including cognitive function evaluation device 100c according to Modification 2 of the present embodiment. In cognitive function evaluation device 100c according to Modification 2 of the present embodiment, body movement sensor 105 is radio wave sensor 300. The characteristic functional configuration of cognitive function evaluation device 100c according to Modification 2 of the present embodiment is substantially identical to that of cognitive function evaluation device 100 of Embodiment 1 illustrated in FIG. 2. Modification 2 is different from Embodiment 1 in the kind of body movement sensor 105, the operation of the calculating unit, and the contents of reference data stored in advance in storing unit 102.

As illustrated in FIG. 19, in order to measure body movement data on subject 2 walking, radio waves are emitted to subject 2 and are detected using multiple radio wave sensors 300. Radio wave sensors 300 are connected so as to be communicable with cognitive function evaluation device 100c via cable 400.

Radio wave sensor 300 is a sensor for detecting a moving body with a Doppler module. For example, radio wave sensor 300 emits microwaves. Microwaves emitted from radio wave sensor 300 hit subject 2 through a space and reflect from subject 2. The reflected microwaves are detected by radio wave sensor 300. At this point, if subject 2 moves while reflecting microwaves, a frequency change (Doppler shift) occurs according to the moving speed of subject 2 between microwaves emitted by radio wave sensor 300 and microwaves detected by radio wave sensor 300.

The calculating unit may calculate a frequency difference (difference between emitted radio waves and detected radio waves) caused by the Doppler effect during walking of subject 2, so that the calculating unit may calculate, for example, relative position data or acceleration data by detecting a motion of subject 2 in each direction during walking. In other words, the calculating unit calculates the periodicity of a body movement of subject 2 walking from a frequency difference between microwaves emitted by radio wave sensor 300 and microwaves detected by radio wave sensor 300. The calculating unit identifies the cognitive function level of subject 2 by checking data on the calculated periodicity of the body movement against reference data stored in storing unit 102 so as to correspond to the data on the periodicity.

[Effects]

For the cognitive function evaluation device according to the present embodiment, body movement sensor 105 for detecting body movement data from subject 2 walking may be acceleration sensor 10, camera 200, or radio wave sensor 300.

Thus, the cognitive function evaluation device according to the present embodiment can quickly identify the cognitive function level of subject 2 regardless of the kind of body movement sensor 105.

(Others)

The cognitive function evaluation device and the cognitive function evaluation method according to the embodiments were described. The present invention is not limited to the embodiments.

For example, in the present embodiment, the calculating unit of the cognitive function evaluation device is implemented as software by executing programs by means of a processor. The present invention is not limited to this method of implementing the calculating unit. The calculating unit may be implemented as hardware by using a dedicated electronic circuit including a gate array or the like.

Moreover, the cognitive function evaluation device according to the present embodiment identified the cognitive function level of subject 2 from the integral of the frequency spectrum, a step length, or the time of a step, that is, walking data on subject 2. In this case, it is not necessary to separately calculate the integral of the frequency spectrum, a step length, and the time of a step, that is, data on the periodicity of a body movement of subject 2 walking. In other words, the cognitive function level of subject 2 may be identified by optionally combining the integral of the frequency spectrum, a step length, and the time of a step of subject 2.

For example, the calculating unit multiplies the integral of the frequency spectrum, a step length, and the time of a step by a predetermined numeric value in advance as a weight. The calculating unit calculates the integral of the frequency spectrum, a step length, and the time of a step from body movement data on subject 2. In this case, the calculating unit assigns stored weights to the calculation result. The calculating unit further adds up the integral of the frequency spectrum, the step length, and the time of a step with the assigned weights. After the addition of the integral of the frequency spectrum, the step length, and the time of a step with the assigned weights, the cognitive function level may be identified by checking the result of addition against the reference data.

Furthermore, the cognitive function evaluation device according to the present embodiment identified one of ND, MCI, and AD as a specific example of the specification of the cognitive function level. However, the cognitive function evaluation device according to the present embodiment is not limited to the specification of one of ND, MCI, and AD. For example, the degree of intoxication of subject 2 may be identified.

In the present embodiment, Alzheimer's disease was discussed as a specific example of a deterioration of the cognitive function. The cognitive function means the capability of cognition, memorization, and decision. Dementia indicates a deterioration of the cognitive function. The cognitive function level to be identified by the cognitive function evaluation device according to the present embodiment is not limited to Alzheimer's disease and may be, for example, vascular dementia.

Moreover, in the present embodiment, data on the relationship between MoCA test scores and the periodicity of body movements is stored in advance as reference data in storing unit 102 in order to identify the cognitive function level of subject 2. However, the reference data is not limited to data on the relationship between the MoCA test and the periodicity of body movements as long as the cognitive function is identified by checking the reference data against the periodicity of body movements. For example, the reference data may be data on the relationship between the scores of MMSE (Mini-Mental State Examination) and the periodicity of body movements.

In Embodiments 1 and 2, camera 200 and radio wave sensor 300 are connected so as to communicate with the cognitive function evaluation device via cable 400 but the communication method is not limited. For example, camera 200 and radio wave sensor 300 may each include a radio communication device and communicate with cognitive function evaluation device 100 via the radio communication device. Acceleration sensor 10 transmits the measured acceleration data to cognitive function evaluation device 100 via radio communications. Radio communications may be conducted based on predetermined radio communications standards, for example, Bluetooth (registered trademark), Wi-Fi (registered trademark), and ZigBee (registered trademark).

The present invention may be implemented as a program that enables a computer to perform the steps to be performed by the cognitive function evaluation device. The present invention may be implemented as a non-transitory recording medium, e.g., a CD-ROM readable by a computer where the program is recorded. Alternatively, the present invention may be implemented as information on the program, data, or a signal. The program, information, data, and signal may be delivered via communication networks such as the Internet.

Additionally, the present invention includes a configuration implemented by modifying the embodiments in various ways by a person skilled in the art or a configuration implemented by optionally combining the constituent elements and functions of the embodiments without departing from the scope of the present invention.

The invention claimed is:

1. A cognitive function evaluation device, comprising:
a storing unit configured to store reference data on a relationship between periodicity of a body movement of a person walking and a cognitive function level of the person;
an acquiring unit configured to acquire body movement data on a detected body movement from a body movement sensor configured to detect the body movement of a subject walking; and
a calculating unit configured to calculate, in real time while the subject is walking, the periodicity of the body movement from the body movement data acquired by the acquiring unit and check the calculated periodicity of the body movement against the reference data stored in the storing unit so as to identify the cognitive function level corresponding to the calculated periodicity of the body movement, wherein
the calculating unit is configured to calculate the periodicity of the body movement, which is the frequency component of any finite range, wherein the range includes at least 6 Hz, the frequency of at least 6 Hz being a frequency component at a frequency higher than a frequency for walking, the calculating unit calculating an integral at a frequency higher than the frequency for walking as the periodicity of the body movement,
the periodicity of the body movement is indicative of a cognitive impairment in the subject,
the body movement data is data on a change in the body movement over time,
the calculating unit is configured to output an evaluation result indicating the identified cognitive function level and to display the evaluation result, the evaluation result including an image indicating the cognitive function level,
the body movement data is data on a change in acceleration of the body movement over time,
the calculating unit is further configured to generate relative position data on a movement of a center of gravity position of the subject from the body movement data and, identify a time period, during which the subject makes a predetermined number of steps while walking, based on the generated relative position data and calculate the step length from the body movement data in the identified time period, the identified time period being a time period after a predetermined time has passed after the subject starts walking, and perform frequency analysis on the body movement data in the identified time period, and
the calculating unit is configured to predetermine the predetermined time.

2. The cognitive function evaluation device according to claim 1, wherein the body movement data is data on a change in an acceleration of the subject over time in a horizontal direction orthogonal to a walking direction in which the subject is walking.

3. The cognitive function evaluation device according to claim 1, wherein the body movement sensor is an acceleration sensor, a camera, or a radio wave sensor.

4. A cognitive function evaluation method comprising:
acquiring, by a device, body movement data on a detected body movement from a body movement sensor configured to detect the body movement of a subject walking; and
calculating, by the device and in real time while the subject is walking, periodicity of the body movement from the body movement data acquired in the acquiring and identifying a cognitive function level corresponding to the calculated periodicity of the body movement by checking the calculated periodicity of the body movement against reference data that is stored in a storing unit and indicates a relationship between the periodicity of the body movement of a person walking and a cognitive function of the person,
wherein the device calculates the periodicity of the body movement, which is the frequency components of any finite range, wherein the range includes at least 6 Hz,
wherein the at least 6 Hz is a frequency component at a frequency higher than a frequency for walking, the periodicity of the body movement being indicative of a cognitive impairment in the subject,
the device calculating an integral at a frequency higher than the frequency for walking as the periodicity of the body movement,
the body movement data is data on a change in the body movement over time,
the device configured to output an evaluation result indicating the identified cognitive function level and to display the evaluation result, the evaluation result including an image indicating the cognitive function level,
the body movement data is data on a change in acceleration of the body movement over time,
the device is further configured to generate relative position data on a movement of a center of gravity position of the subject from the body movement data and, identify a time period, during which the subject makes a predetermined number of steps while walking, based on the generated relative position data and calculate the step length from the body movement data in the identified time period, the identified time period being a time period after a predetermined time has passed after the subject starts walking, and perform frequency analysis on the body movement data in the identified time period, and the device is configured to predetermine the predetermined time.

5. A non-transitory computer-readable recording medium having recorded thereon a program for enabling a computer to implement the cognitive function evaluation method according to claim 4.

6. A cognitive function evaluation device, comprising:

a storing unit configured to store reference data on a relationship between periodicity of a body movement of a person walking and a cognitive function level of the person;

an acquiring unit configured to acquire body movement data on a detected body movement from a body movement sensor configured to detect the body movement of a subject walking; and a calculating unit configured to calculate, in real time while the subject is walking, the periodicity of the body movement from the body movement data acquired by the acquiring unit and check the calculated periodicity of the body movement against the reference data stored in the storing unit so as to identify the cognitive function level corresponding to the calculated periodicity of the body movement, wherein the periodicity of the body movement is a step length of the subject walking, the body movement data is data on a change in the acceleration of the body movement over time, the calculating unit is further configured to generate relative position data on a movement of a center of gravity position of the subject from the body movement data and, identify a time period, during which the subject makes a predetermined number of steps while walking, based on the generated relative position data and calculate the step length from the body movement data in the identified time period, the identified time period being a time period after a predetermined time has passed after the subject starts walking, based on the step length calculated, the calculating unit is further configured to identify a cognitive function level of the person, the cognitive function level being indicative of a cognitive impairment in the subject, and the calculating unit is configured to predetermine the predetermined time.

7. A cognitive function evaluation device, comprising:

a storing unit configured to store reference data on a relationship between periodicity of a body movement of a person walking and a cognitive function level of the person;

an acquiring unit configured to acquire body movement data on a detected body movement from a body movement sensor configured to detect the body movement of a subject walking; and a calculating unit configured to calculate, in real time while the subject is walking, the periodicity of the body movement from the body movement data acquired by the acquiring unit and check the calculated periodicity of the body movement against the reference data stored in the storing unit so as to identify the cognitive function level corresponding to the calculated periodicity of the body movement, wherein the periodicity of the body movement is a time taken for the subject to take one step when walking, the body movement data is data on a change in the acceleration of the body movement over time, the calculating unit is further configured to generate relative position data on a movement of a center of gravity position of the subject from the body movement data and, after a predetermined time has passed after the subject starts walking, identify a time period, during which the subject makes a predetermined number of steps while walking, based on the generated relative position data and calculate the time of a step from the body movement data in the identified time period, the identified time period being a time period after a predetermined time has passed after the subject starts walking, based on the time of the step calculated, the calculating unit is further configured to identify a cognitive function level of the person, the cognitive function level being indicative of a cognitive impairment in the subject, and the calculating unit is configured to predetermine the predetermined time.

* * * * *